(12) United States Patent
Croud et al.

(10) Patent No.: US 8,034,766 B2
(45) Date of Patent: *Oct. 11, 2011

(54) COMPOSITIONS AND METHODS FOR PRION DECONTAMINATION

(75) Inventors: Vincent Brian Croud, Suffolk (GB); John Collinge, London (GB); Graham Jackson, Oxon (GB)

(73) Assignees: E I du Pont de Nemours and Company, Wilminton, DE (US); University College London, London (GB)

( * ) Notice: Subject to any disclaimer, the term of this patent is extended or adjusted under 35 U.S.C. 154(b) by 842 days.

This patent is subject to a terminal disclaimer.

(21) Appl. No.: 11/977,844

(22) Filed: Oct. 26, 2007

(65) Prior Publication Data
US 2008/0206843 A1    Aug. 28, 2008

Related U.S. Application Data

(60) Provisional application No. 60/925,177, filed on Apr. 19, 2007, provisional application No. 60/854,831, filed on Oct. 27, 2006.

(51) Int. Cl.
*C07K 14/00* (2006.01)

(52) U.S. Cl. ............... 514/2; 530/300; 424/94.2

(58) Field of Classification Search ............... None
See application file for complete search history.

(56) References Cited

U.S. PATENT DOCUMENTS

| | | | |
|---|---|---|---|
| 4,456,544 A | 6/1984 | Lupova et al. | |
| 4,749,511 A | 6/1988 | Lad et al. | |
| 4,822,512 A | 4/1989 | Auchincloss | |
| 5,234,832 A | 8/1993 | Disch et al. | |
| 5,500,364 A | 3/1996 | Christianson et al. | |
| 5,624,634 A | 4/1997 | Brougham et al. | |
| 5,677,272 A * | 10/1997 | Ghosh et al. ............... | 510/306 |
| 6,214,366 B1 | 4/2001 | Prusiner et al. | |
| 6,479,454 B1 | 11/2002 | Smith et al. | |
| 6,506,589 B1 | 1/2003 | Hastrup et al. | |
| 6,534,036 B1 | 3/2003 | Collinge et al. | |
| 6,555,355 B1 | 4/2003 | Hansen et al. | |
| 6,558,938 B1 | 5/2003 | Hansen et al. | |
| 6,558,939 B1 | 5/2003 | Nørregaard-Madsen et al. | |
| 6,605,458 B1 | 8/2003 | Hansen et al. | |
| 6,613,505 B2 | 9/2003 | Shih | |
| 6,632,646 B1 | 10/2003 | Aaslyng et al. | |
| 6,682,924 B1 | 1/2004 | Sierkstra et al. | |
| 6,720,371 B2 | 4/2004 | Furuta et al. | |
| 6,773,907 B2 | 8/2004 | Hansen et al. | |
| 6,777,218 B1 | 8/2004 | Mikkelsen et al. | |
| 6,780,629 B2 | 8/2004 | Hansen et al. | |
| 6,780,979 B1 | 8/2004 | Deslys | |
| 6,808,913 B2 | 10/2004 | Hastrup et al. | |
| 6,835,821 B2 | 12/2004 | Hastrup et al. | |
| 6,893,855 B2 | 5/2005 | Nørregaard-Madsen et al. | |
| 6,921,657 B2 | 7/2005 | Hansen et al. | |
| 7,015,037 B1 | 3/2006 | Furcht et al. | |
| 7,026,531 B1 | 4/2006 | Bilyeu | |
| 7,098,017 B2 | 8/2006 | von der Osten et al. | |
| 7,109,016 B2 | 9/2006 | Outtrup et al. | |
| 7,550,420 B2 * | 6/2009 | DiCosimo et al. ............ | 510/226 |
| 2001/0027182 A1 | 10/2001 | Zoghbi et al. | |
| 2001/0032339 A1 | 10/2001 | Zoghbi et al. | |
| 2002/0172989 A1 | 11/2002 | Shih | |
| 2002/0192731 A1 | 12/2002 | Shih | |
| 2003/0049249 A1 | 3/2003 | Weissmann et al. | |
| 2003/0050276 A1 | 3/2003 | Cunanan et al. | |
| 2003/0073592 A1 | 4/2003 | McDonnell et al. | |
| 2004/0005283 A1 | 3/2004 | Prusiner et al. | |
| 2004/0091474 A1 | 5/2004 | Raven et al. | |
| 2004/0106188 A1 | 6/2004 | Kritzler et al. | |
| 2004/0110669 A1 | 6/2004 | Kakkis | |
| 2004/0115730 A1 | 6/2004 | O'Connor | |
| 2005/0032188 A1 | 2/2005 | Shih | |
| 2005/0255095 A1 | 11/2005 | Kakkis | |
| 2006/0030505 A1 | 2/2006 | Biering et al. | |
| 2006/0040846 A1 * | 2/2006 | Hoyt et al. ................ | 510/499 |
| 2006/0105930 A1 | 5/2006 | McDonnell et al. | |
| 2006/0127390 A1 | 6/2006 | Hoglund et al. | |
| 2006/0134092 A1 | 6/2006 | Miwa et al. | |
| 2006/0147499 A1 | 7/2006 | Oestergaard et al. | |
| 2006/0217282 A1 | 9/2006 | Jackson et al. | |
| 2006/0228696 A1 | 10/2006 | Rohwer et al. | |
| 2007/0037723 A1 | 2/2007 | McDonnell et al. | |

(Continued)

FOREIGN PATENT DOCUMENTS

DE    3741583    6/1988

(Continued)

OTHER PUBLICATIONS

Carter et al., Engineering Subtilisin BPN' for Site-Specific Proteolysis; Proteins: Structure, Function, and Genetics (1989), 6, 240-248; Alan R. Liss, Inc.

(Continued)

*Primary Examiner* — Anand Desai

(57) ABSTRACT

The invention relates to compositions and methods for prion degradation, decontamination or disinfection. The composition comprises an oxidizing agent, one or more proteases and a surfactant such as an ionic surfactant/detergent. The method comprises contacting a prion contaminated entity with a prion-degrading composition comprising an effective amount of an oxidizing agent, an effective amount of at least one protease, and an effective amount of a surfactant. The components of the composition may be contacted with a prion-contaminated entity sequentially or simultaneously using an aqueous composition. Typically at least two different proteases are used for optimal efficacy. Preferably the oxidizing agent comprises peracetyl ions or a source thereof. The invention also relates to kits comprising the various reagents.

3 Claims, 11 Drawing Sheets

U.S. PATENT DOCUMENTS

2007/0105740 A1 5/2007 Dicosimo et al.

FOREIGN PATENT DOCUMENTS

| DE | 19822406 | | 11/1999 |
|---|---|---|---|
| DE | 20021445 | | 6/2001 |
| DE | 10106594 | | 8/2002 |
| DE | 10203225 | | 7/2003 |
| EP | 0 733 369 | A1 | 9/1996 |
| EP | 0 736 302 | A2 | 10/1996 |
| EP | 1 088 059 | B1 | 4/2004 |
| EP | 1464334 | A1 | 10/2004 |
| GB | 2 348 203 | A | 9/2000 |
| GB | 2 394 663 | A | 5/2004 |
| JP | 2004 195361 | | 7/2004 |
| WO | WO 00/51624 | | 9/2000 |
| WO | WO 02/17974 | A1 | 3/2002 |
| WO | WO02/47484 | A1 | 6/2002 |
| WO | WO 02/053723 | A2 | 7/2002 |
| WO | WO 03/031552 | A1 | 4/2003 |
| WO | WO 2004/003505 | A2 | 1/2004 |
| WO | WO 2004/039418 | A1 | 5/2004 |
| WO | WO 2005/092114 | A2 | 10/2005 |
| WO | WO 2006/016145 | A1 | 2/2006 |
| WO | WO 2006/076045 | A1 | 7/2006 |
| WO | WO 2006/119060 | A1 | 11/2006 |

OTHER PUBLICATIONS

Cho, Inactivation of the Scrapie Agent by Pronase; Can J Comp Med (1983), 47(4), 494-496.

Darbord et al., Inactivation of prions in daily medical practice, Biomed & Pharmacother 1999; 53; 34-38.

Fichet et al., Novel methods for disinfection of prion-contaminated medical devices; The Lancet (2004), 364, 521-26.

Glickman et al., The Ubiquitin-Proteasome Proteolytic Pathway: Destruction for the Sake of Construction; Physiological Reviews (2002), 82(2), 373-428, American Physiological Society, U.S.A.

Hwang et al., Semiquantitative Calculations of Catalytic Free Energies in Genetically Modified Enzymes; Biochemistry (1987), 26, 2669-2673; The American Chemical Society, U.S.A.

Jackson et al., An enzyme-detergent method for effective prion decontamination of surgical steel; J. of General Virology (2005), 86, 869-878; Great Britain.

Jacobs et al., Cloning, sequencing and expression of subtilisin Carlsberg from Bacillus liceniformis; Nucleic Acids Research (1985), 13(24), 8913-8926; IRL Press Limited, Oxford, England.

Klöhn et al., A quantitative, highly sensitive cell-based infectivity assay for mouse scrapie prions; Proceedings of the National Academy of Sciences of the United States of America (PNAS) (2003), 100(20), 11666-11671; U.S.A.

Kurihara et al., Subtilisin Amylosaccharicticus, J. of Biological Chemistry (1972), 247(17), 5619-2631, U.S.A.

Langveld et al., Enzymatic Degradition of Prion Protein in Brain Stem from Infected Cattle and Sheep; J. of Infectious Diseases (2003), 188, 1782-1789; Infectious Diseases Society of America, U.S.A.

McLeod et al., Proteolytic inactivation of the bovine spongiform encephalopathy agent; Biochemical and Biophysical Research Communications (2004), 317, 1165-1170, Elsevier.

Meloun et al., Complete primary structure of thermitase from *Thermoactinomyces vulgaris* and its structural features related to the subtilisin-type proteinases; Federation of European Biochemical Societies (Apr. 1985), 183(2), 195-200, Elsevier Science Publishers B.V. (Biomedical Division).

Peretz et al., Inactivation of Prions by Acidic Sodium Dodecyl Sulfate; J. of Virology (2006), 80(1), 322-331, American Society for Microbiology.

Prusiner et al., Scrapie agent contains a hydrophobic protein; Proc. Natl. Acad. Sci. USA (1981), 78(11), 6675-6679.

Rao et al., Molecular and Biotechnological Aspects of Microbial Proteases; Microbiology and Molecular Biology Reviews (Sep. 1998), 597-635; American Society for Microbiology, U.S.A.

Siezen et al., Subtilases: The superfamily of subtilisin-like serine proteases; Protein Science (1997), 6, 501-523; Cold Spring Harbor Laboratory Press, U.S.A.

Svendsen et al., Complete amino acid sequence of alkaline mesentericopeptidase; Federation of European Biochemical Societies (Feb. 1986), 196(2), 228-232; Elsevier Science Publishers B.V. (Biomedical Division).

Takagi, Protein Engineering on Subtilisin, Int. J. Biochem. (1993), 25(3), 307-312; Pergamon Press, Ltd., Great Britain.

Taylor, Inactivation of prions by physical and chemical means; J. of Hospital Infection (1999), 43 (Supplement): S69-S76; The Hosptial Infection Society, United Kingdom.

Tindbaek et al., Engineering a substrate-specific cold-adapted subtilisin; Protein Engineering, Design & Selection (2004), 17(2), 149-156; Oxford University Press, Great Britain.

Vasantha et al., Genes for Alkaline Protease and Neutral Protease from *Bacillus amyloliquefaciens* Containing a Large Open Reading Frame Between the Regions Coding for Signal Sequence and Mature Protein; J. of Bacteriology (1984), 159(3), 811-819; American Society for Microbiology, U.S.A.

von der Osten et al., Protein engineering of subtilisins to improve stability in detergent formulations; J. of Biotechnology (1993), 28, 55-68; Elsevier Science Publishers B.V. (Biomedical Division).

Wadsworth et al., Tissue distribution of protease resistant prion protein in variant Creutzfeldt-Jakob disease using a highly sensitive immunoblotting assay; The Lancet (Jul. 21, 2001), 358, 171-180.

Wells et al., Cloning, sequencing, and secretion of *Bacillus amyloliquefaciens* subtilisin in *Bacillus subtilis*; Nucleic Acids Research (1983), 11(22), 7911-7925; IRL Press Limited, Oxford, England.

Wells et al., Designing substrate specificity by protein engineering of electrostatic interactions; Proceedings of the National Academy of Sciences of the United States of America (PNAS) (1987), 84, 1219-1223; U.S.A.

WHO Infection Control Guidelines for Transmissible Spongiform Encephalopathies; Report of a WHO consultation, Geneva, Switzerland, Mar. 23-26, 1999.

* cited by examiner

Time   0   5   10   30   60   120 min 0   5   10   30   60   120 min

COMPOSITIONS AND METHODS FOR PRION DECONTAMINATION

This application claims the benefit of U.S. Provisional Patent Application No. 60/854,831, filed Oct. 27, 2006, and U.S. Provisional Patent Application No. 60/925,177, filed Apr. 19, 2007.

FIELD OF THE INVENTION

The present invention relates to methods and reagents for use in prion decontamination. In particular, the invention relates to prion decontamination of surgical instruments, advantageously avoiding autoclaving.

BACKGROUND OF THE INVENTION

The persistence and resistance of the prion agents responsible for CJD (Creutzfeldt-Jakob disease) has raised fears about the possibility of iatrogenic transmission following surgery. The prion diseases, which include scrapie, atypical scrapie in sheep, BSE (Bovine Spongiform Encephalopathy) in cattle, CWD (Chronic Wasting Disease) in deer and CJD in humans are a novel group of transmissible, fatal neurodegenerative conditions. The transmissible agent termed a prion is comprised largely or solely of a conformational isomer of a normal cellular $PrP^C$ prion protein. The disease related conformer, designated $PrP^{Sc}$, has several unusual properties including resistance to proteolysis, detergent insolubility and high thermal stability. These physical properties coupled to observations that $PrP^{Sc}$ adheres strongly to surgical steel and other materials present problems in the cleaning and sterilisation of surgical instruments as prion infectivity is known to be resistant to conventional autoclaving.

In the absence of a pre-clinical diagnostic test for CJD, pre-surgical testing of patients is not possible. Although in a minority of cases where CJD is suspected or confirmed, used instruments can be quarantined or destroyed. However, for the majority of procedures, new methods of decontamination are required. There are many ongoing efforts, including those by the UK Department of Health (e.g. Medical Research Council (MRC) Prion Unit, London, UK), attempting to address the problem of iatrogenic CJD transmissions.

Standard autoclaving, and in some cases high temperature autoclaving to 134° C., is the hospital standard for prion decontamination. However, conventional studies have shown survival of prions under autoclave conditions (Taylor, D M., *J. Hosp. Infect.* 43:S69-S76 (1999); Jackson et al., *J. Gen. Virol* 86:869-878 (2005)). Clearly prions will gradually accumulate under these conditions. Even the most effective autoclave will only sterilize to the degree that heat and steam penetrate the articles being treated. This is not straightforward when dealing with surgical sets comprising numerous complex instruments.

Taylor (Taylor D. M., supra) discloses the use of sodium hypochlorite solutions and 2M sodium hydroxide in prion inactivation. However, there are problems with this approach such as incomplete inactivation and incompatibility with many medical devices. Furthermore, resistance of prions to autoclaving is reported.

The WHO (World Health Organization) guidelines on prion decontamination recommend autoclaving and immersing contaminated instruments in 1M NaOH and/or 20,000 ppm NaOCl (WHO report "Infection Control Guidelines for Transmissible Spongiform Encephalopathies", Mar. 23-26 1999, Geneva, Switzerland, WHO/CDS/CSR/APH/2000.3). This is an extremely hazardous procedure and can leave undesirable salt residues on surfaces. Furthermore, in addition to the safety aspects, the corrosive effect of such alkali or oxidizing halogen species at that concentration, combined with the temperatures and pressures implicit to autoclaving, would be likely to destroy or at least seriously damage delicate surgical instruments.

Commercial reagents currently in use for cleaning of surgical instruments prior to autoclaving have little or no effect upon $PrP^{Sc}$ contamination. Existing methods of decontamination such as those involving LPH® and LPH®se (Steris, Inc. Mentor, Ohio), and Endozyme Plus (Ruhof Corp., Mineola, N.Y.) are of limited use in destroying infectivity. Furthermore, some reagents are incompatible with medical materials such as Dracom polymer (polysulfone).

Fichet et al. (*Lancet* 364:521-526 (2004)) describe three methods for disinfection of prion contaminated medical devices. Firstly they describe use of an enzymatic cleaner (KLENZYME®, Merck & Co., Inc., Whitehouse Station, N.J.) with autoclaving at 121° C. Secondly they describe alkaline cleaner (HAMO™ 100 PID, Steris, Mentor, Ohio). The third method described is the only one said to be suitable for fragile devices such as endoscopes and involves use of the alkaline cleaner on wet instruments followed by a dry vaporized hydrogen peroxide (VHP) treatment. Fichet et al. also disclose enzymatic cleaner followed by VHP treatment as being very effective. There is no disclosure of the composition of the enzymatic cleaner. Peracetic acid is used and shown to be ineffective (100% onward transmission rate following treatment).

The present invention seeks to overcome problem(s) associated with the prior art by providing effective prion decontamination compositions and methods.

SUMMARY OF THE INVENTION

An aqueous prion-degrading composition is provided comprising a combination of active reagents including an effective amount of an oxidizing agent, at least one protease, and an effective amount of surfactant that can be used for effective prion degradation (i.e. to reduce the titre of infective prions) of a prion-contaminated entity. Preferably, the prion-degrading composition further comprises an effective amount of an ionic surfactant. Surprisingly, the oxidizing agent and protease enzyme combination provides a synergistic effect on prion decontamination.

An aqueous prion-degrading composition is also provided comprising (a) an effective amount of at least one oxidizing agent; (b) an effective amount of at least one first protease; (c) an effective amount of at least one second protease wherein said second protease is different from said at least one first protease; and (d) an effective amount of a surfactant.

In a preferred embodiment, the aqueous prion-degrading composition comprises two proteases selected from the group consisting of NEUTRASE®, ALCALASE®, PRONASE®, and Proteinase K. In a further preferred embodiment, the two proteases are NEUTRASE® and ALCALASE®.

In a preferred embodiment, the surfactant is sodium dodecyl sulfate (SDS).

In another embodiment, the aqueous prion-degrading composition further comprises an additional ingredient selected from the group consisting of pH adjusters, buffering agents, chelating agents, corrosion inhibitors, peroxygen stabilizers, and mixtures thereof.

The present invention further provides methods by which prion-contaminated entities such as medical instruments can be decontaminated of prion infectivity. According to the methods of this invention, the prion-contaminated entity is contacted with the components of the aqueous prion-degrading composition sequentially or simultaneously. Simultaneous contact is highly preferred.

It has surprisingly been found that the methods of this invention result in the potentiating of activity of the components of the prion-degrading composition, resulting in improvements in prion decontamination. In particular use of the oxidizing agent in combination with the proteases described below result in a synergistic effect.

In one embodiment, a method for prion decontamination or disinfection is provided which comprises: (a) contacting a prion-contaminated entity with at least one surfactant; (b) contacting the entity with an oxidizing agent, and (c) contacting the entity with at least one protease.

In a particular embodiment there is provided a sequential method for prion decontamination or disinfection of a prion-contaminated entity which comprises: (a) first contacting the entity to be decontaminated with a surfactant, and then (b) contacting the entity to be decontaminated with an oxidizing agent, and then (c) contacting the entity with a protease.

In another embodiment, a method for prion decontamination or disinfection of a prion-contaminated entity comprises: (a) first contacting the entity with a surfactant, and then (b) contacting the entity with an oxidizing agent, and then (c) contacting the entity with a first protease, and (d) contacting the entity with a second protease.

In another embodiment, a method for degrading prion particles is provided comprising, (a) providing an aqueous prion-degrading composition comprising (i) an effective amount of at least one oxidizing agent; (ii) at least one first protease; (iii) at least one second protease wherein the second protease is different from the at least one first protease, and (iv) an effective amount of a surfactant; (b) contacting a prion-contaminated entity with the prion-degrading composition of (a) under suitable conditions whereby prion particles are degraded.

In another embodiment, the proteases and the oxidizing agent are contacted simultaneously with the entity to be decontaminated. In this embodiment, the surfactant may be contacted with the entity with the proteases and the oxidizing agent or the surfactant may be contacted with the entity in a separate step.

In a preferred embodiment, the two proteases are selected from the group consisting of NEUTRASE®, ALCALASE®, PRONASE®, and Proteinase K. In a further preferred embodiment, the two proteases are NEUTRASE®, and ALCALASE®.

The prion-contaminated entity can have a solid surface or be a fluid, such as a biological fluid. Solid surfaces include medical and dental instruments. In one aspect, the prion-contaminated entity is selected from the group consisting of a biological waste, equipment used in food processing equipment, an enclosure used to house animals, a medical instrument, a dental instrument, and countertops. Food processing includes, for example, slaughterhouses and poultry-processing facilities. In a preferred embodiment, the prion-contaminated entity is selected from the group consisting of prion-contaminated medical instruments. In another preferred aspect, the medical instrument is an endoscope or laparoscope. In yet another aspect, the medical instrument is comprised of steel, plastic or a combination thereof. The medical instrument may also be comprised of other materials of construction typically found in medical devices and instruments.

In another aspect, the prion-degrading methods and compositions are used to decrease and/or eliminate iatrogenic CJD.

In a preferred aspect, the methods for prion decontamination are performed in a medical instrument sterilizer.

In another aspect, any of the methods of the present invention further comprise and preferably have as a final step, autoclaving the prion-contaminated entity.

In one preferred aspect, the present method is used for low temperature decontamination where autoclaving is avoided.

In another embodiment, a kit is provided which comprises: (a) a first reagent comprising an oxidizing agent; (b) a second reagent comprising at least one protease; and (c) a third reagent comprising a surfactant.

In a preferred embodiment, the second reagent in the kit comprises at least two different proteases. In a preferred embodiment, the two proteases are selected from the group consisting of NEUTRASE®, ALCALASE®, PRONASE®, and Proteinase K. In a further preferred embodiment, the two proteases are NEUTRASE® and ALCALASE®.

In another preferred embodiment, the first, second, and third reagents are provided individually as solids. In a preferred embodiment, the first, second, and third reagents of the kit are provided as solid powders.

In another embodiment, the kit further comprises an additional reagent selected from the group consisting of pH adjusters, buffering agents, chelating agents, corrosion inhibitors, peroxygen stabilizers and mixtures thereof, which may be supplied as additional kit reagent or may be included as an reagent in one or more of the first, second, and third reagents.

DETAILED DESCRIPTION OF THE INVENTION

Figure 1A:
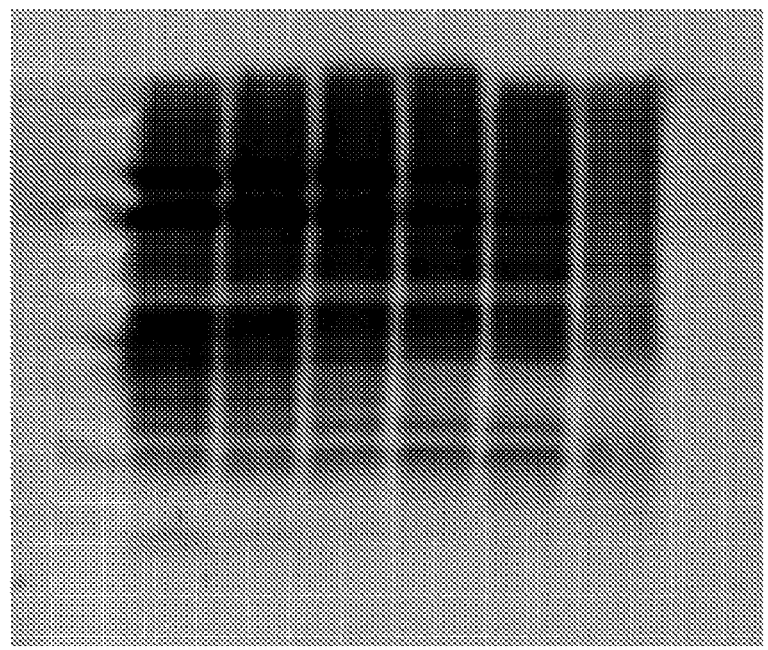
FIGS. 1a and 1b. Western blot analyses of the data generated in Example 2 showing the no detectable efficacy of PERASAFE™ Sterilant for decontamination of prions (FIG. 1a) as compared to combined treatment with PERASAFE™ Sterilant and proteases and SDS (FIG. 1b), wherein decontamination was exhibited.

The invention provides a prion-decontaminating composition, methods for prion decontamination and a kit for use in decontaminating and prion-contaminated entity.

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures;

through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In a further embodiment, "about" means the referenced value within 10%, preferably within 5%, and most preferably within 1%.

As used herein, the terms "prion" and "prion particles" refer to a proteinaceous disease-causing agent responsible for a number of degenerative brain diseases in animals and humans. Examples of prion-associated diseases include, but are not limited to Creutzfeldt-Jakob Disease (all forms including CJD, iCJD (iatrogenic), vCJD (variant), sCJD (sporadic), and familial (fCJD)), Gerstmann-Sträussler-Scheinker Syndrome, Fatal Familial Insomnia, and Kuru. Examples of prion-associated diseases in animals include, but are not limited to scrapie, atypical scrapie in sheep, BSE (Bovine Spongiform Encephalopathy) in cattle, and CWD (Chronic Wasting Disease) in deer.

As used herein, the term "prion contaminated surface" refers to a surface contaminated with (or potentially contaminated with) an infective prion particle.

As used herein, "effective amount" is used to describe the amount of a particular substance or combination of substances within a formulation described herein to achieve a decrease in the titre of infective prion particles.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0 and will also include both the protonated and unprotonated (i.e. peracetyl ions) forms.

As used herein, the term "perhydrolysis" is defined as the reaction of a selected substrate (an "activator") with peroxide to form a peracid. Typically, inorganic peroxide is reacted with the activator to produce the peracid. In one embodiment, the peracid is peracetic acid.

As used herein, the term "biological contaminants" refers to one or more unwanted and/or pathogenic biological entities including, but not limited to microorganisms, spores, viruses, prions, and mixtures thereof. The present invention is particularly effective in destroying and/or degrading prions.

As used herein, the term "disinfect" refers to the process of destruction of or prevention of the growth of biological contaminants. As used herein, the term "disinfectant" refers to a composition that disinfects by destroying, neutralizing, or inhibiting the growth of biological contaminants. Typically, disinfectants are used to treat inanimate objects or surfaces.

As used herein, the term "decontaminate" means to make safe by eliminating harmful substances (e.g. prions particles).

As used herein, the terms "peroxygen source", "source of peroxygen", and "oxygen source" refer to compounds capable of providing and effective amount of hydrogen peroxide including, but not limited to hydrogen peroxide, hydrogen peroxide adducts (e.g., urea-hydrogen peroxide adduct (carbamide peroxide)), perborates, and percarbonates. In a preferred embodiment, the peroxygen source is sodium perborate.

As used herein, the term "oxidizing agent system" refers a system (e.g. a composition or formulation) that provides an effective amount of an oxidizing agent. In one embodiment, the oxidizing agent system comprises a peroxygen source and a peracid activator that (when mixed under suitable aqueous reaction conditions) generates an efficacious amount of peracid, preferably peracetic acid.

Aqueous Prion-Degrading Composition

The present invention relates to compositions for use in prion decontamination of prion-contaminated entities. In one aspect, the invention provides a prion-degrading composition comprising an oxidizing agent, one or more proteases and a surfactant such as an ionic surfactant/detergent.

Oxidizing Agent

The oxidizing agent may be any chemical entity or mixture capable of oxidizing (or of catalysing the oxidation of) proteins, preferably prion protein(s).

The oxidizing agent may be any of those known to be effective in formulations with biocidal efficacy. The oxidizing agent may be selected from the group consisting of peroxide, persalt, peracids, persulfates, peroxyphthalates, organic chlorines, chlorine dioxide, and stable mixtures thereof. Examples include sodium hypochlorite, sodium perborate, sodium percarbonate, hydrogen peroxide, peracetic acid, chlorine dioxide, potassium peroxymonopersulfate, sodium dichloroisocyanurate, trichlorocyanuric acid, and stable mixtures thereof.

In one embodiment, the oxidizing agent is provided as a liquid or a solid dissolved in a polar solvent (e.g., water). Once dissolved, the oxidizing agent provides a suitable concentration of active oxidizing agent species in the prion-degrading composition. "Active oxidizing agent" refers to total oxidizing species as determined by available oxygen AVOX/iodometric titration, or other suitable method (thiosulfatimetric method, permanganometric method, cerimetric method), that is, oxidizing power (see "Peroxide Chemistry", Waldemar Adam, Editor, Wiley-VCH, Weinheim, Germany, 2001 and "Organic Peroxides", Daniel Swern, Editor, John Wiley and Sons, Inc., Hoboken, N.J., 1971). In the iodometric method, the oxidizing power of products is conveniently measured in terms of the amount of iodine liberated by reaction with potassium iodide (determined by a subsequent titration of that iodine). The procedure is standard in the art, and the results can be expressed in terms of available hypohalite, peracid, of halogen, or of oxygen, or simply as "oxidizing power".

Preferred oxidizing agents are those with good low temperature efficacy and good materials compatibility.

In a preferred embodiment, the oxidizing agent comprises peroxide, a modified peroxide, a peracid, such as peracetic acid, or mixtures thereof. This maybe an equilibrium mixture of peracetic acid, hydrogen peroxide and acetic acid or generated in situ from an appropriate source of peroxygen and an "activator". Examples of activators (or peracid precursors) include, but are not limited to tetraacetylethylenediamine (TAED), nonanoyloxybenzene sulfonate (NOBS), Sodium nonanoyloxybenzene sulfonate (SNOBS), nonyl amido caproyl oxybenzene sulfonate (NACA-OBS), carboxylic acid esters, triacetin, diacetin, acetic acid, tetracetyl glycol uril (TAGU), diacetyl hexahydrotriazine oxide, N-acyl lactams, acetyl triethyl citrate (ACT), glucose pentaacetate, sucrose octaacetate, and acetyl salicylic acid, to mention a few. In a preferred embodiment, the activator is an N-acyl donor, such as TAED, SNOBS, TAGU, N-acyl lactams. In a further preferred aspect, the activator is TAED.

It will be recognised that the peracetic acid and peroxide will exist in both protonated and de-protonated forms, the ratio being dependent on the pH and the pKa of the relevant species. Examples of commercially available peracid-based disinfectants include, but are not limited to PERASAFE™ Sterilant and RELYON™ Disinfectant. PERASAFE™ Sterilant is a powdered blend of an oxygen source (40-60 wt % sodium perborate and 10-30 wt % tetraacetylethylene diamine), stabilizer, corrosion inhibitor, buffer, and surfactant, that when mixed with water, generates an oxidizing agent system comprising approximately 0.26% peracetic acid (as a mixture of peracetic acid and peracetyl ions) at pH 8.0, when prepared according to manufacturer's instructions.

Preferably the oxidizing agent is a peroxygen system. A peroxygen system is a combination of peroxygen source (e.g., a persalt such as sodium perborate or sodium percarbonate) and an activator such as tetraacetyl ethylenediamine (TAED) or N-acetyl caprolactam, or other activator as listed hereinabove, which generates peracetic acid and peracetic anions in situ upon dissolution. Preferably, the peroxygen system is used in the liquid phase, preferably in solution, preferably in aqueous solution.

In a one aspect, the oxidizing agent comprises at least one C1 to C10 aliphatic peracid. In a preferred aspect, the oxidizing agent comprises peracetyl ions ($CH_3C(O)OO^-$) and/or peracetic acid ($CH_3C(O)OOH$; CAS 79-21-0). Preferably the oxidizing agent comprises hydrogen peroxide and/or peracetic acid, more preferably the oxidizing agent comprises hydrogen peroxide, peracetic acid and peracetyl ions. A preferred oxidizing agent is PERASAFE™ Sterilant as supplied by Antec International, Sudbury, UK (a subsidiary of E. I. DuPont de Nemours and Company, Inc., Wilmington, Del., USA). In a particular embodiment, PERASAFE™ Sterilant is formulated for a stock solution ranging from 0.1× to 20× PERASAFE™ Sterilant, preferably from 0.5× to 5× PERASAFE™ Sterilant, more preferably 0.5× to 2× PERASAFE™ Sterilant. In case of conflict, preferably PERASAFE™ Sterilant is formulated in accordance with the manufacturers' instructions, i.e., 81 g/5 litres for a 1× PERASAFE™ Sterilant stock solution.

The amount of oxidizing agent in the aqueous prion-degrading composition is an effective amount, i.e., an amount that, when used in the composition with the other components is effective for prion degradation. Preferably, when the oxidizing agent is peracetic acid, it is used at a concentration equivalent to 0.26 w/v % peracetic acid (0.26% arises from use of PERASAFE™ Sterilant at 16.2 g/L so that 0.1% remains 24 hours after make up). It has been surprisingly discovered that there is synergy between the oxidizing agent and the protease (prion-degrading enzyme) used herein. Thus, reduced use of the oxidizing agent can be offset by increased use of enzyme and vice versa. The exact amounts of both oxidizing agent and protease can be determined by in-use conditions, cost considerations and the degree of efficacy required. These amounts can be readily determined by one skilled in the art.

Preferably the oxidizing agent is used at near-neutral pH. In one embodiment, the pH range is about 5 to about 9, preferably about 6 to about 8, and most preferably about 8 for reasons of materials compatibility.

Optionally, hydrogen peroxide is also included in the oxidizing composition in addition to other oxidizing agent. Preferably hydrogen peroxide is in solution, more preferably in aqueous solution.

Optionally, acetic acid is also included in the oxidising composition.

Proteases

The aqueous prion-degrading composition comprises at least one protease that, when combined with the oxidizing agent, is present in an amount effective for prion degradation.

Proteases or peptidases (used interchangeably) are enzymes which cleave the amide linkages in protein substrates (see Walsh, *Enzymatic Reaction Mechanisms*, W.H. Freeman and Company, San Francisco, Chapter 3 (1979) and Rao et al., *Microbiol. Mol. Biol. Rev.*, 62(3):597-635 (1998)). Proteases includes any enzyme belonging to the EC 3.4 enzyme group, as defined by the Nomenclature Committee of the International Union of Biochemistry and Molecular Biology. These enzymes can be grossly subdivided into two major categories, exopeptidases and endopeptidases, depending upon their site of action.

As proteases are ubiquitous to all living organisms, suitable prion-degrading proteases for use in the composition of this invention can be isolated from a variety of eukaryotic and/or prokaryotic organisms. Commercially-useful proteases have been isolated from plants (e.g. papain, bromelain, and keratinases), animals (e.g., trypsin, pepsin, and rennin), and microbes such as fungi (e.g., *Aspergillus oryzae* proteases) and bacteria (especially well-known proteases isolated from the genus *Bacillus*). *Bacillus* species secrete two extracellular types of protease, neutral proteases (many of which are metallo-endoproteases, such as NEUTRASE®, typically active in a general pH range of about 5 to about 8, see U.S. Pat. No. 6,636,526) and alkaline proteases (such as ALCALASE®, typically characterized by high activity at alkaline pH; see GENBANK® P00780 and P00782; van der Osten et al., *J. Biotechnol.*, 28:55-68 (1993)).

A sub-group of the serine proteases tentatively designated subtilases has been proposed by Siezen, et al., supra. These serine proteases are useful in the composition, method and kit of this invention. They are defined by homology analysis of more than 40 amino acid sequences of serine proteases previously referred to as subtilisin-like proteases. A subtilisin was previously defined as a serine protease produced by Gram-positive bacteria or fungi, and according to Siezen, et al., now is a subgroup of the subtilases (or "subtilisin proteases"). A wide variety of subtilisins have been identified, and the amino acid sequence of a number of subtilisins have been determined. These include more than six subtilisins from *Bacillus* strains, namely, subtilisin 168, subtilisin BPN', subtilisin Carlsberg, subtilisin Y, subtilisin amylosaccharaticus, and mesentericopeptidase (Kurihara et al., *J. Biol. Chem.* 247 5629-5631 (1972); Wells et al., *Nucleic Acids Res.* 11 7911-7925 (1983); Stahl and Ferrari, *J. Bacteriol.* 159 811-819 (1984), Jacobs, et al., *Nucl. Acids Res.* 13 8913-8926 (1985); Nedkov et al., *Biol. Chem. Hoppe-Seyler* 366 421-430 (1985), Svendsen, et al., *FEBS Lett.* 196 228-232 (1986)), one subtilisin from an actinomycetales, thermitase from *Thermoactinomyces vulgaris* (Meloun et al., *FEBS Lett.* 198 195-200 (1985)), and one fungal subtilisin, Proteinase K from *Tritirachium album* (Jany and Mayer, *Biol. Chem. Hoppe-Seyler* 366 584-492 (1985)). For further reference, see Table I from Siezen, et al., supra.

Subtilisins are well-characterized physically and chemically. In addition to knowledge of the primary structure (amino acid sequence) of these enzymes, over 50 high resolution X-ray structures of subtilisins have been determined which delineate the binding of substrate, transition state, products, at least three different protease inhibitors, and define the structural consequences for natural variation (Kraut, *Ann. Rev. Biochem.* 46 331-358 (1977)).

One subgroup of particularly useful subtilases for this invention, I-S1, comprises the "classical" subtilisins, such as subtilisin 168, subtilisin BPN', subtilisin Carlsberg (e.g., ALCALASE®, available from Novozymes A/S, Bagsvaerd, Denmark), and subtilisin DY.

A further subgroup of the subtilases I-S2, is recognized by Siezen, et al. (supra). Sub-group I-S2 proteases are also useful proteases in this invention and are described as highly alkaline subtilisins and comprise enzymes such as subtilisin PB92 (e.g., MAXACAL®, Gist-Brocades NV, Denmark), subtilisin 309 (e.g., SAVINASE®, Novozymes), subtilisin 147 (e.g., ESPERASE®, Novozymes), and alkaline elastase YaB.

Random and site-directed mutations of the subtilase gene have both arisen from knowledge of the physical and chemical properties of the enzyme and contributed information relating to subtilase's catalytic activity, substrate specificity, tertiary structure, etc. (Wells, et al., *Proc. Natl. Acad. Sci. U.S.A.* 84:1219-1223 (1987); Wells, et al., *Phil. Trans. R. Soc. Lond.*A. 317:415-423 (1986); Hwang and Warshel, *Biochem.* 26 2669-2673 (1987); Rao, et al., *Nature* 328:551-554 (1987); Carter, et al., *Proteins* 6:240-248 (1989); Graycar, et al., *Annals of the New York Academy of Sciences* 672 71-79 (1992); and Takagi, *Int. J. Biochem.* 25 307-312 (1993).

Examples of proteases and protease variants which are useful in this invention have been disclosed in numerous United States patents and patent applications including, but not limited to U.S. patent application publications U.S. 20050239188A1 and U.S. 20060147499A1 and issued U.S. patents: U.S. Pat. No. 5,500,364; U.S. Pat. No. 6,506,589; U.S. Pat. No. 6,555,355; U.S. Pat. No. 6,558,938; U.S. Pat. No. 6,558,939; U.S. Pat. No. 6,605,458; U.S. Pat. No. 6,632,646; U.S. Pat. No. 6,682,924; U.S. Pat. No. 6,773,907; U.S. Pat. No. 6,777,218; U.S. Pat. No. 6,780,629; U.S. Pat. No. 6,808,913; U.S. Pat. No. 6,835,821; U.S. Pat. No. 6,893,855; U.S. Pat. No. 6,921,657; U.S. Pat. No. 7,026,53; U.S. Pat. No. 7,098,017; and U.S. Pat. No. 7,109,016.

Examples of commercially available proteases include, but are not limited to the group consisting of *Bacillus* sp. (e.g. *Bacillus subtilis*, *Bacillus amyloliquefaciens*, *Bacillus licheniformis*, *Bacillus lentus*, etc.), proteases such as subtilisins (ALCALASE®; available from Novozymes A/S, Bagsvaerd, Denmark), the neutral protease NEUTRASE® (available from Novozymes), EVERLASE® (Novozymes; a protease from *Bacillus* sp. available from Sigma-Aldrich, catalog #P5985), POLARZYME® (Novozymes; a protease engineered for low temperature washing applications), SAVINASE® (available from Novozymes), *Sus scrofa* pepsin, *Carica papaya* chymopapain, *Ananas comosus* bromelain, *Carica papaya* papain, *Streptomyces griseus* PRONASE® (also known as PRONASE E® or PRONASE®), *Tritirachium album* Proteinase K (including recombinantly-produced Proteinase K from *Pichia pastoris*), and mixtures thereof. These proteases are commercially available enzymes and may be available in a variety of product forms including powders, tablets, and liquid formulations. In another aspect, the commercially-available enzymes(s) may be optionally purified or partially purified prior to use in the present formulations. Means to purify proteins are well-known in the art. In a preferred embodiment, the protease is selected from the group consisting of Proteinase K, PRONASE®, ALCALASE®, NEUTRASE®, and mixtures thereof.

In one aspect, the composition of this invention comprises a combination of two or more proteases. Preferably when two or more proteases are present in the composition, the proteases are selected from the group consisting of PRONASE®, proteinase K, ALCALASE®, and NEUTRASE®.

In a preferred embodiment, the protease is a combination of Proteinase K and PRONASE®, ALCALASE® and NEUTRASE® or ALCALASE® and PRONASE®. When the composition comprises two or more proteases, the proteases can be used sequentially or simultaneously in a mixture for proteolysis. However, it should be noted that when contacting a prion-contaminated entity with several proteases at once, individual activities can be reduced and compensation might be necessary e.g., by longer time of contact. This is discussed in more detail below.

As is plain to a person of ordinary skill in the art, the higher the concentration of protease(s), the greater and more rapid destruction is achieved. Combinations of protease concentration and time may be chosen according to need. These can be optimised by routine trial and error.

Proteases are susceptible to genetic and/or peptide or chemical level manipulation or modification. It will be apparent to a person skilled in the art that truncations, mutations or adaptation of the proteases (e.g., to make them more protease resistant themselves) does not interfere with the invention provided that the peptidase activity of the enzyme(s) is retained by such manipulation(s). (Indeed, it is accepted that PRONASE® is more in the nature of a fractionated protease preparation rather than a recombinantly purified enzyme, and use of a sub-fractionation product of PRONASE® or of a cloned and recombinantly purified fraction of the peptidase (s) comprised by PRONASE® are embraced by the present invention). Thermostable proteases are particularly preferred, whether obtained by modification of existing proteases or by cloning proteases from thermophilic organisms.

In general, total protease, added to the composition of the invention is about 1.6 g/l (1.6 mg/mL). However, an effective amount of protease can and will vary, for example, from less than 0.1 to over 20 g/l, depending on the amount of oxidizing agent present. Typical ranges are from 0.1 to 5 g/l or from 1 to 4 g/l. More protease will be added if less oxidizing agent is present and conversely, less protease may be used in an effective composition if more oxidizing agent is present.

Surfactant/Detergent

The prion-degrading composition of the present invention comprises a surfactant. As used herein, the terms "surfactant" and "detergent" will be used interchangeably and include zwitterionic surfactants, anionic surfactants, cationic surfactants, and non-ionic surfactants. Examples of surfactants include, but are not limited to anionic surfactants such as sodium dodecyl sulfate (SDS), ammonium lauryl sulfate and other alkyl sulfate salts, sodium 1-octanesulfonate monohydrate, N-lauroylsarcosine sodium salt, sodium lauryl sulfate, sodium lauryl ether sulfate (SLES), sodium taurodeoxycholate hydrate, and alkyl benzene sulfonate; cationic surfactants such as cetyl trimethylammonium bromide and other alkyltrimethylammonium salts, cetylpyridinium chloride, polyethoxylated tallow amine, benzalkonium chloride, and benzethonium chloride; zwitterionic (amphoteric) surfactants such as dodecyl betaine, dodecyl dimethylamine oxide, cocamidopropyl betaine, and coco ampho glycinate; and non-ionic surfactants such as alkyl poly(ethylene oxide), copolymers of poly(ethylene oxide) and poly(propylene oxide, alkyl polyglucosides (e.g., acetyl glucoside), decyl maltoside, fatty alcohols, cetyl alcohol, oleyl alcohol, cocamide monoethanolamine, cocamide diethanolamine, and cocamide triethanolamine).

In a particular embodiment the surfactant is selected from the group consisting of sodium dodecylbenzene sulfonate, lauryl ether sulfate, ethylene oxide/propylene oxide alkyl phenol condensate, polyglycol ether of fatty alcohols, fatty acid ethylene oxide condensate, polyglycol ether of alkyl phenols, fatty alcohol ethoxylate, sodium lauryl ether sulfate, sodium dodecyl sulfate, and combinations of two or more thereof.

In another particular embodiment, the surfactant is a cationic or anionic surfactant, preferably an anionic surfactant, and more preferably sodium dodecyl sulfate (SDS), sodium taurodeoxycholate hydrate, sodium 1-octanesulfonate monohydrate, lithium dodecyl sulphate, N-lauroylsarcosine sodium salt, or a combination of two or more thereof. Preferably the surfactant is SDS.

The surfactant can be used at any effective concentration. This may be easily determined and/or optimised by routine trial and error. When the surfactant is SDS, the final concentration of the surfactant with regard to the contacting a prion-contaminated entity with a surfactant is preferably about 1% (weight percent) to about 6%, more preferably about 1% to about 3%, even more preferably about 1%, and most preferably 1%, based on Western Blot optimization. Again, there is synergy between the enzymes, surfactant and oxidizing agent and the component levels can be varied to fit use requirements.

Proteases can be adversely affected (e.g., suffer reduced activity or loss of activity) in the presence of excess surfactant. Individual proteases have individual characteristics, and it is well within the abilities of a person skilled in the art to avoid loss of activity due to surfactant action. Manufacturers' guidance should be followed wherever possible. Advantageously surfactant level(s) are limited so as not to significantly inhibit protease activity for prion-degradation before and at the time of contact with protease.

Additional Components

In a preferred embodiment, the prion-degrading composition comprises at least one corrosion inhibitor. Although the corrosion inhibitor may not contribute to the efficacy of the prion-degrading composition, use of at least one corrosion inhibitor is preferred, especially when decontaminating delicate instruments. Examples of corrosion inhibitors are described in U.S. Pat. No. 5,077,008 and typically include, but are not limited to triazoles (e.g., benzotriazole), azoles, phosphates, and benzoates. In one embodiment the corrosion inhibitor is benzotriazole or tolyltriazole. In a preferred embodiment, the corrosion inhibitor is benzotriazole.

In another preferred embodiment, the prion-degrading composition comprises at least one peroxygen stabilizer. Peroxygen stabilizers are known, see for example, U.S. Pat. No. 5,624,634. Examples of peroxygen stabilizers suitable for use in the composition of this invention include hydrogen peroxide stabilizers and peracid stabilizers. Such stabilizers include, but are not limited to, amino tri(methylene phosphonic acid) (DEQUEST® 2000 series), 1-hydroxyethylidene-1,1-diphosphonic acid (HEDP; DEQUEST® 2010 series), hexamethylene diamine tetramethylene phosphonic acid (DEQUEST® 2050 series), bis hexamethylene triamine penta methylene phosphonic acid (DEQUEST® 2090 series, diethylenetriamine pentamethylene phosphonate (DEQUEST®) 2060 series), ethylene diamine tetramethylene phosphonic acid (DEQUEST® 2041), dipicolinic acid, phosphonic acids and salts thereof. DEQUEST stabilizers are available from Solutia, Inc., St. Louis, Mo. In a preferred embodiment, the peroxygen stabilizer is ethylene diamine tetramethylene phosphonic acid (DEQUEST® 2041) or 1-hydroxyethylidene-1,1-diphosphonic acid (HEDP, DEQUEST® 2010) and/or salts thereof.

Preferred Embodiments

In one preferred embodiment the prion-degrading composition comprises at least two proteases. In one embodiment, the prion-degrading composition comprises at least two proteases and the surfactant is sodium dodecyl sulfate. In a further preferred embodiment, the two proteases are selected from the group consisting of PRONASE®, ALCALASE®, NEUTRASE®, and Proteinase K and the surfactant is sodium dodecyl sulfate. More preferably, the prion-degrading composition comprises two proteases and the two proteases are NEUTRASE® and ALCALASE®.

Preferably the oxidizing agent of the prion-degrading composition comprises peracetic acid at pH from about 6 to about 8, and hence consists of both protonated and deprotonated forms.

Method for Decontaminating Prion-Infected Entity

The present invention provides a method for decontaminating a prion-contaminated entity which comprises contacting the contaminated entity with (a) an effective amount of at least one oxidizing agent, (b) an effective amount of at least one protease, and (c) and effective amount of at least one surfactant. The contacting step is performed for a period of time sufficient to degrade the prion particles. Preferred oxidizing agents, proteases, surfactants and their amounts for use in the methods of this invention are described hereinabove.

The method optionally comprises the step of autoclaving the entity after contacting with the prion-degrading composition. The protocol for use of the prion-degrading composition is compatible with existing hardware such as machines used for pre-washing medical instruments prior to autoclaving.

In one embodiment, at least one oxidizing agent and at least two protease steps are used in combination with a surfactant.

In another aspect the invention relates to a method as described above wherein the first protease is NEUTRASE® and the second protease is ALCALASE®.

Simultaneous/Sequential Contacting

The contacting steps of the method of this invention can be performed sequentially or simultaneously. Preferably, the prion-contaminated entity is contacted with the at least one protease either simultaneously with or following contact with the oxidizing agent.

Where more than one protease is used, the proteases may be combined into a single step. However, protease activity can be lowered in such an embodiment due to each protease digesting the other. Still, the individual steps in the methods of the present invention may be carried out sequentially or simultaneously. The steps of the methods of this invention may be repeated and any of the methods may further comprise washing steps to remove the prion-degrading composition, e.g., from a solid surface.

When the contacting steps are performed sequentially, the method of this invention comprises (a) first contacting the prion-contaminated entity with a surfactant, and then (b) contacting the entity with an oxidizing agent, and then (c) contacting the entity with at least one protease.

In another embodiment, a sequential method for prion decontamination or disinfection of a prion-contaminated entity comprises: (a) first contacting the entity with a surfactant, and then (b) contacting the entity with an oxidizing agent, and then (c) contacting the entity with a first protease, and (d) contacting the entity with a second protease. When contacting the prion-contaminated entity with two proteases, it may be advantageous to remove all or a portion of the first protease before the entity is contacted with the second protease. In one embodiment, substantially all of the first protease is removed before contact with the second protease. This applies equally to each protease step in a multi-step sequence.

In one embodiment, it may be further desirable to separate the surfactant application step from the protease application step(s) if the surfactant adversely affects the protease activity. In this embodiment, at least a proportion of the surfactant is removed (or diluted) before the entity is contacted with a protease in order to maximize protease activity.

In a preferred embodiment, an aqueous prion-degrading composition comprising an effective amount of oxidizing agent, an effective amount of at least two proteases, and an effective amount of at least one surfactant, are combined and simultaneously contacted with a prion-contaminated entity, i.e., in a single step. Thus, the surfactant is mixed together with the protease and the oxidizing agent, preferably immediately prior to use so that a single aqueous composition is applied to the prion-contaminated entity. In this embodiment, a lower temperature (see below) is typically used to avoid inactivation of the enzymes (proteases).

In a further preferred embodiment, all of the components of the prion-degrading composition are mixed together in water to form a single aqueous prion-degrading composition which is subsequently contacted with a prion-contaminated entity.

Alternatively, in one embodiment, the surfactant is contacted with the prion-contaminated entity prior to contacting the entity simultaneously with the oxidizing agent and the proteases.

In a preferred aspect the invention provides a method for prion decontamination comprising simultaneously contacting a prion-contaminated entity with a surfactant, an oxidizing agent, NEUTRASE® and ALCALASE® to provide a reaction mixture. Preferably the surfactant is SDS. Optionally, the method further comprises, after the contacting step, autoclaving the reaction mixture.

Whether sequential or simultaneous method is employed, the reaction time or incubation time for each step will typically be less than 24 hours, preferably less than 2 hours, more preferably less than 1 hour, and most preferably less than 20 minutes.

Autoclaving

In one aspect the invention, the method of this invention further comprises, autoclaving the entity.

Autoclaving, if employed as described herein, can be carried out following any suitable autoclave cycle. Typical cycles include 121° C. for 18 minutes or preferably 134° C. for 18 minutes. Alternative cycles may be chosen by the operator to suit their particular needs. Extended autoclave cycles may be advantageously employed. Autoclaving in water can enhance the prion destructive effects and is therefore preferred where autoclaving is used.

Advantageously an autoclaving step is performed as a final step in the methods of the present invention, that is, autoclaving is performed after contacting step(s). An autoclaving step provides the advantage of minimizing spread of infection via the prion-contaminated entity, and is particularly advantageous when the entity is a surgical instrument. Furthermore, by combining contacting step(s) with autoclaving in this manner, there may advantageously be a multiplicative increase in efficacy, i.e., if each method can reduce infectious titre by 5 logs then combining them may reduce infectivity by even more, such as by 10 logs.

Preferably autoclaving is avoided or performed for reduced time such as less than 3 hours, preferably autoclaving is omitted; especially for fragile medical instruments.

Temperature

The prion-degrading composition and its individual components, such as, in a sequential method, can be contacted with the prion-contaminated entity over a range of temperatures. In one embodiment, the contacting step(s) is at a temperature in the range of 15° C. to about 80° C., preferably about 20° C. to about 60° C., more preferably about 40° C. to about 60° C., and most preferably about 45° C. to about 55° C.

When contacting the surfactant in a separate step that does not include a protease, the surfactant may be contacted with the prion-contaminated entity at any suitable temperature. Indeed, a high temperature may be used. A separate step for contacting surfactant with the entity is flexible and is preferably performed at a temperature of at least 70° C., preferably at least 80° C., preferably at least 90° C., preferably at least 100° C.

The temperature may be constrained by the nature of the entity, for example some medical equipment such as endoscopes cannot tolerate high temperatures such as those used in autoclaving. For these situations, the methods of the invention advantageously do not involve autoclave conditions, and the temperature choice should be made by the operator with regard to the tolerances of the entity being decontaminated. Examples of methods according to the present invention which avoid the use of autoclave conditions may be found in the Examples section. Advantageously methods according to the present invention such as those in the Examples may replace conventional prior art treatments such as LPH®, LPH®se, and EndozymePlus treatment. See, U.S. Patent Application Publication No. 200610217282 A1.

Whether sequential or simultaneous method is employed, the reaction time or incubation time for each step will typically be less than 24 hours, preferably less than 2 hours, more preferably less than 1 hour, and most preferably less than 20 minutes.

Incubation temperatures, that is, temperatures at which the protease(s) are contacted with the entity will vary according to the protease used. Generally, any temperature from room temperature (e.g., 15-20° C.) up to about 80° C. is acceptable, wherein about 20° C. to about 60° C. is more preferred, wherein about 40° C. to about 60° C. is even more preferred, and about 45° C. to about 55° C. is most preferred. As the temperature moves away from the optimum for a particular protease, deactivation of the prion contaminants takes longer. Clearly, this can be compensated for by incubating for a longer time or using a greater concentration of protease. At temperatures above 60° C. activities can be lower and the enzymes can become inactivated, but clearly individual protease preparations will have individual deactivation temperatures and the manufacturers' guidance should be followed wherever possible.

As used herein, "low temperature" means less than 134° C., preferably less than 121° C., more preferably less than 100° C., even more preferably less than 90° C., even more preferably less than 80° C., even more preferably less than 70° C., yet even more preferably less than 60° C., and most preferably means a temperature such as about 35° C. to about 60° C.

Miscellaneous Method Features

Preferably, the contacting step(s) is carried out with agitation. Preferably said agitation is a rotary agitation, e.g., at about 750 rpm.

Examples presented herein include conditions optimal for use in automated washing machines. Furthermore, the conditions chosen are advantageously low in cost.

Advantageously, when the prion-contaminated entity is a medical instrument, the methods for prion decontamination are performed in a medical instrument sterilizer.

Prion-Contaminated Entity

The prion-contaminated entity may be any physical item for which it is desired to deactivate and/or remove prions. The term embraces fluids as well as solids (objects) such as devices or medical instruments (including surgical instruments). Fluids include biological fluids. The prions to be deactivated or removed may be in the entity (e.g., in solution or suspension in a fluid), or may be on the entity (e.g., bound, attached or otherwise associated with a surface of a solid entity). Thus, the entity may have a surface. Entities having surfaces include, for example, a medical instrument, a laboratory instrument, a clean-room surface, a countertop, or the surface of an area or equipment used for food preparation or processing or the surface of an enclosure used to house animals. The surface may comprise metal, plastic or any other relevant material of construction. The metal may be steel such as surgical steel.

When the prion-contaminated entity is a solid surface, it may also be laboratory countertops, laboratory instruments and laboratory equipment, for example in a clean room for research, production and testing of pharmaceutical and biological compounds.

Non-limiting examples of entities, which may be contaminated with prions and which can be advantageously and effectively decontaminated according to the methods of this invention, include surgical equipment surfaces from veterinary or hospital settings as wells as surfaces that come in contact with said surgical equipment. Preferably the entity is a medical instrument, including fragile instruments, such as a laparoscope or endoscope.

The entity may be used in the food processing industry. Thus, prion-contaminated entity may be selected from the group consisting of tanks, conveyors, floors, drains, coolers, freezers, equipment surfaces, walls, valves, belts, pipes, drains, joints, crevasses, and combinations of two or more thereof. The prion-contaminated entity may be selected from a surface of a barn or stable for livestock, such as poultry, cattle, dairy cows, goats, horses and pigs; and or hatcheries and hatcheries for poultry or shrimp.

The target surface may be contacted with the present prion-decontaminating compositions using any number of means. The time, temperature, and effective concentration used when contacting the desired locus can be easily determined by one of skill in the art. Specific contacting methods include spraying, treating, immersing, flushing, pouring on or in, mixing, combining, painting, coating, applying, affixing to and otherwise communicating the present prion-decontaminating composition(s) with the surface to be treated, i.e., known or suspected of being contaminated with prion particles.

Decontamination

Decontamination refers to reduction in prion titre in a specific sample or setting. Decontamination may refer to the removal of prions from a surface whether or not said prions are deactivated. Thus, decontamination includes deactivation and also includes the elimination of prions without regard to whether or not they are destroyed/deactivated. When decontaminating, it is important that prion infectivity is removed from the surface or solution being decontaminated. This may be by destruction (deactivation) or by simple separation. Thus, the methods of this invention may further comprise, after contacting the prion-contaminated entity with (a) an effective amount of at least one oxidizing agent, (b) an effective amount of at least one protease, and (c) and effective amount of at least one surfactant, separating the treated entity from the treating reagents. The important aspect is that prions (i.e., $PrP^{Sc}$) are no longer associated with the surface or solution being decontaminated or are reduced in number and/or titre. Clearly, if non-infective prion fragments remain adhered to a treated surface after decontamination, this would not materially affect the decontamination or the fact that the surface had been successfully decontaminated.

In one aspect of this invention, the prion-degrading compositions and methods are used to decrease and/or eliminate iatrogenic CJD.

Decontamination may be assessed by any suitable assay. Preferably, the assay used is Western Blotting or bioassay. Clearly assays such as bioassays and/or Western Blotting assays have a sensitivity limit. So long as prion titre (prion number/infectivity) has been reduced, then prion decontamination will be considered to have taken place.

Preferably prion decontamination is 100 fold, preferably 1000 fold, preferably 10,000 fold, preferably 100,000 fold, preferably 1,000,000 fold or even more. Preferably prions are completely eliminated or deactivated.

Disinfection refers to cleansing so as to destroy or prevent the growth of pathogenic microorganisms in addition to the decontamination associated with prion infectivity. The disinfection occurs by the combined action of an effective amount of oxidizing agent (e.g., peracetic acid), an effective amount of the protease(s), and an effective amount of the surfactant.

Assay Methods

The reduction in prions produced by the methods of the present invention may be monitored by any suitable means known in the art. Specific examples of suitable assay techniques are provided herein to illustrate the assessment of prion reduction.

Clearly, certain methods will present themselves as more suitable for a given situation than other methods. For example, if prion decontamination is taking place in solution, then a Western Blotting approach might be most suitable. If prion decontamination is taking place on a surface, then direct visualisation on that surface might be most suitable. Alternatively for prion decontamination taking place on a surface, bioassay might be the most suitable. Choice of individual assay methods for individual situations is well within the capabilities of a person skilled in the art. It will be appreciated that in many situations the most important indicator is loss/reduction of infectivity. Currently, prion infectivity is most usually assessed by bioassay. However, biochemical assay of the infective conformer $PrP^{Sc}$ is equally appropriate.

An example of a suitable monitoring method is an immunoblotting assay. Advantageously the immunoblotting assay is, or is based on, the assay described in Wadsworth et al. (*Lancet* 358:171-180 (2001)).

An example of a suitable monitoring method is a bioassay. Bioassay methods are generally geared towards the individual prion species being assayed. Selection of suitable bioassay methods is advantageously based on the prion species being assayed.

Kits

The present invention also relates to kits for use in decontamination of prion-contaminated entities. In one embodiment, the kit comprises a set of reactants wherein a first reactant comprises an oxidizing agent, a second reactant comprises at least one protease and a third reactant comprises a surfactant.

In a preferred embodiment the second reactant comprises at least two proteases. In a more preferred embodiment, the at least one or the at least two proteases are selected from the group consisting of PRONASE®, Proteinase K, ALCALASE®, and NEUTRASE®. In a more preferred embodiment, the second reactant comprises at least two proteases, wherein the two proteases are ALCALASE®, and NEUTRASE®.

In a further embodiment, the kit comprises one or more additional reactants wherein the additional reactants are selected from the group consisting of pH adjusters, buffering agents, chelating agents, corrosion inhibitors, peroxygen stabilizers and mixtures thereof. Alternatively, the first, second or third reactant may further comprise one or more of the additional reactants.

In a further embodiment, each of the reactants in the kit are supplied in solid form, preferably as powders, to promote storage stability. The reactants of the kit are mixed with a polar solvent at an effective concentration of each of the reactants. Once effectively mixed in the polar solvent there is provided a prion-decontaminating composition ready to use. The preferred polar solvent is water.

The reagents used are water soluble, stable, and of low toxicity. The protocol for their use is compatible with existing hardware for example as used in hospital decontamination departments for pre-washing and autoclaving instruments. Thus the invention provides for decontamination of prion infectivity from surgical instruments. Advantageously the methods of the present invention can be implemented using existing machinery.

The invention is now illustrated by way of examples which should not be regarded as limiting in scope. In particular the step(s) in the Examples wherein an entity is treated with a surfactant at high temperature is (are) not to be regarded as essential features of the invention, but is (are) merely advantageous optional steps.

Various modifications and variations of the described methods and compositions of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

EXAMPLES

Example 1

Combined Oxidation and Protease Treatment

This example describes methods by which an entity contaminated with the infectious material $PrP^{Sc}$ can be decontaminated and the infectious material deactivated in an aqueous suspension by sequential exposure of the entity (in the example the entity is infected brain tissue) to an oxidizing agent plus SDS as surfactant and two proteolytic enzymes (ALCALASE® and NEUTRASE®).

Preparation of Tissue Samples:

Brain of CJD-infected human frontal cortex was homogenized to 20% (w/v) in PBS Dulbecco GIBCO-BRL 14190-094 (Paisley, UK), phosphate buffer solution, referred to hereinafter as "PBS", by passing the brain tissue through 18-gauge, 21-gauge and 23-gauge needles to produce "homogenate". The homogenate was diluted to 15% w/v with PBS, frozen in small aliquots and stored at −70° C.

Protocol A: Use of ALCALASE®/NEUTRASE® Concentrations in the Presence of PERASAFE™ Sterilant Each reaction was performed at a total volume of 100 µL, containing 60 µL of 10% w/v brain homogenate.

(a) A sample of brain homogenate, 60 µL of 10% w/v brain homogenate, was contacted with 20 µL of 5× oxidizing agent PERASAFE™ Sterilant, prepared according to manufacturer's instructions for a 0.26% peracetic acid concentration at pH 8.0 using phosphate buffered saline solution (PBS), and 5 µL of 20% w/v SDS. The resulting reaction mixture contained PERASAFE™ Sterilant and 1% w/v SDS.

(b) The reaction mixture was incubated at 50° C. for 10 minutes and 40 µL of the reaction mixture was analysed.

(c) Treatment with a first protease: ALCALASE® (Novozymes). A solution of 10 mg/mL ALCALASE® was prepared in water. A 3 µL aliquot of this enzyme solution was added to the 85 µL solution of treated homogenate produced by step (b) above. The final concentration of ALCALASE® was 300 µg/mL.

(e) Treatment with a second protease: NEUTRASE® (Novozymes). A solution of 10 mg/mL NEUTRASE® was prepared in water. A 12 µL aliquot of this enzyme solution was added to the 88 µL solution of SDS/PERASAFE™ Sterilant and ALCALASE®-treated homogenate produced in step (c) above. The final concentration of NEUTRASE® was 1.2 mg/mL. The mixture was incubated at 50° C. for 10 minutes.

Detection of $PrP^{Sc}$ by Western Blot

The materials from the SDS/PERASAFE™ Sterilant/ALCALASE®/NEUTRASE® (Protocol A) treatment described above were submitted to Western blot analysis. The blots were visualized using the antibodies ICSM 18 and ICSM 35 to detect any remaining $PrP^{Sc}$ in the samples. Using either antibody, there was no detectable $PrP^{Sc}$. For antibody information and detection methods throughout, see EP934531 A1 and EP1565213. All antibodies described herein can be found by reference to (PCT) Patent Application No PCT/GB99/03617; UK Patent No. GB 2,348,203; Australian Patent No AU 773763; South African Patent No. ZA 2001/3947; and U.S. Pat. No. 6,534,036.

It is clear from this example that the methods of the present invention lead to significant prion decontamination. After treatment according to Protocol A, with oxidizing agent and two proteases, high levels of destruction of PrP were observed at all concentrations of protease as evidenced by a total lack of immunoreactivity, which is equivalent to at least a 1200 fold reduction of infectivity. This estimate is based upon a previously determined detection limit for the specific Western Blotting protocol used (Wadsworth et al., *Lancet* 358(9277): 171-180 (2001)) which is a preferred assay method.

Using this assay method, it was determined that one can readily detect 12 µL of a 10% w/v brain homogenate in the untreated control. The sensitivity of western blotting for PrP is always 10 nl of 10% w/v homogenate. Thus, if 12 µl of 10% w/v homogenate is the starting amount in an experiment and no signal is detectable by Western Blot then there has been a greater than or equal to 1200 fold reduction in PrP.

Example 2

Prion Decontamination Comparison Using PERASAFE™ Sterilant Treatment Only and PERASAFE™ Sterilant and Protease Treatment in a Single Step In this Example, prion decontamination is demonstrated according to the present invention by oxidation using PERASAFE™ Sterilant and protease treatment (Protocol C), compared with ineffective prior art treatment of PERASAFE™ Sterilant only (Protocol B).

Protocol B: PERASAFE™ Sterilant Only Treatment (Comparative)

The following protocol was used to prepare samples treated only with PERASAFE™ Sterilant.

(a) A 5× PERASAFE™ Sterilant stock solution was prepared, 1 mL, by adding 81 mg of PERASAFE™ Sterilant powder to 1 mL of distilled and deionized (dd) $H_2O$ at 37° C. Vortex mixing was used to dissolve the powder and the solution was incubated at 37° C. for 15 minutes.

(b) 300 µL of CJD 10% w/v brain homogenate was prepared and subjected to vortex mixing to ensure even suspension by spinning in a microfuge at minimum speed setting of 1 (80×g) for 1 minute.

(c) 200 µL of supernatant of the brain homogenate was removed and transferred to a clean tube, which had been warmed to 37° C. 65 µL of 5× PERASAFE™ Sterilant stock solution was added and mixed with the homogenate by vortex mixing.

(d) 65 µL of PBS was added to the mixture produced in step (c) mixed under vortex.

(e) A 20 µL aliquot of homogenate mixture from step (d) was removed to a separate tube containing 20 µL of 2× SDS loading buffer and then the separate tube was frozen at −70° C. in approximately 5 minutes.

(f) The mixture remaining from step (d) was incubated at 37° C. with agitation (750 rpm).

(g) Further 20 µL aliquots were removed from the mixture produced in step (d) at times 5, 10, 30, 60 and 120 minutes to separate tubes each containing 20 µL of 2× SDS loading buffer. Each aliquot was frozen at −70° C. in approximately 5 minutes.

(h) All aliquots were thawed simultaneously in a heating block at 100° C. Vortex mixing of the aliquots was timed for every two minutes for a total of 10 minutes and the aliquots were centrifuged at maximum speed in a microfuge (15,000× g).

(i) For each 20 µL aliquot sample, the sample was loaded into a separate well containing 16% acrylamide gel buffered with tris-glycine. The gel was run at 200 volts for 80 minutes. The remaining 20 µL of sample was frozen and stored at −70° C.

(j) The acrylamide-gel treated samples from step (i) were subjected to Western blot analysis onto polyvinylidene fluoride (PVDF) membrane (Imobilon-P) for either 90 minutes at 40 volts or at 15 volts overnight (greater than 12 hours).

(k) The membrane was blocked in 5% milk protein and PBS for 45-60 minutes.

(l) The treated samples were incubated with primary antibody for 1 hour, ICSM35B at 0.2 µg/mL in PBS. 25 mL volume was used for a single membrane.

(m) Blots were then developed according to the STORM® system for gel and blot analysis and blot imaging system (PHOSPHOIMAGER®) system technology, available from Molecular Dynamics, Inc., Sunnyvale, Calif.), for quantification.

Protocol C: Proteolytic Degradation with Proteinase K and PRONASE® in Conjunction with PERASAFE™ Sterilant Oxidation The following protocol was used to prepare samples treated with PERASAFE™ Sterilant in conjunction with Proteinase K (PK) and PRONASE® proteases.

(a) A 5× PERASAFE™ Sterilant stock solution was prepared, 1 mL, by adding 81 mg of PERASAFE™ Sterilant powder to 1 mL of distilled and deionized (dd) $H_2O$ at 37° C. Vortex mixing was used to dissolve the powder and the solution was incubated at 37° C. for 15 minutes.

(b) 300 µL of CJD 10% w/v brain homogenate was prepared and subjected to vortex mixing to ensure even suspension by spinning in a microfuge at minimum speed setting of 1 (80×g) for 1 minute.

(c) 200 µL of supernatant of the brain homogenate was removed and transferred to a clean tube, which had been warmed to 37° C. 65 µL of 5× PERASAFE™ Sterilant stock solution was added and mixed with the homogenate by vortex mixing.

(d) 55 µL of a 20% w/v SDS solution in dd $H_2O$ was added to the mixture produced in step (c) and the resulting mixture was mixed under vortex.

(e) 10 µL of a 10 mg/ml solution of PK in dd $H_2O$ and 10 µL of a 40 mg/mL solution of PRONASE® in dd $H_2O$ were added to the mixture produced in step (d) and the resulting mixture was mixed under vortex.

(f) A 20 µL aliquot of homogenate mixture from step (e) was removed to a separate tube containing 20 µL of 2×SDS loading buffer and then the separate tube was frozen at −70° C. in approximately 5 minutes.

(g) The mixture remaining from step (e) was incubated at 37° C. with agitation (750 rpm).

(h) Further 20 µL aliquots were removed from the mixture produced in step (e) at times 5, 10, 30, 60 and 120 minutes to separate tubes each containing 20 µL of 2×SDS loading buffer. Each aliquot was frozen at −70° C. in approximately 5 minutes.

(i) All aliquots were thawed simultaneously in a heating block at 100° C. Vortex mixing of the aliquots was timed for every two minutes for a total of 10 minutes and the aliquots were centrifuged at maximum speed in a microfuge (15,000× g).

(j) For each 20 µL aliquot sample, the sample was loaded into a separate well containing 16% acrylamide gel buffered with tris-glycine. The gel was run at 200 volts for 80 minutes. The remaining 20 µL of sample was frozen and stored at −70° C.

(k) The acrylamide-gel treated samples from step (i) were subjected to Western blot analysis onto polyvinylidene fluoride (PVDF) membrane (Imobilon-P) for either 90 minutes at 40 volts or at 15 volts overnight (greater than 12 hours).

(l) The membrane was blocked in 5% milk protein and PBST for 45-60 minutes.

(m) The treated samples were incubated with primary antibody for 1 hour, ICSM35B at 0.2 µg/mL in PBST. 25 mL volume was used for a single membrane.

(n) Blots were then developed according to the STORM® system for gel and blot analysis and blot imaging system for quantification.

Alternatively, a 5× PERASAFE™ Sterilant stock solution was prepared by adding 81 mg PERASAFE™ Sterilant powder to 1 mL of dd $H_2O$ at 37° C. with vortex mixing to dissolve.

Figure 1B:
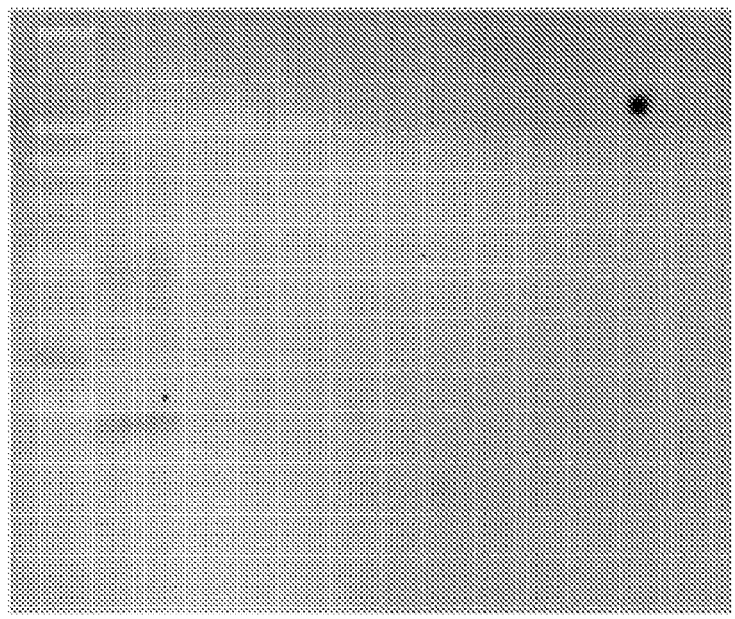
Figure 2:
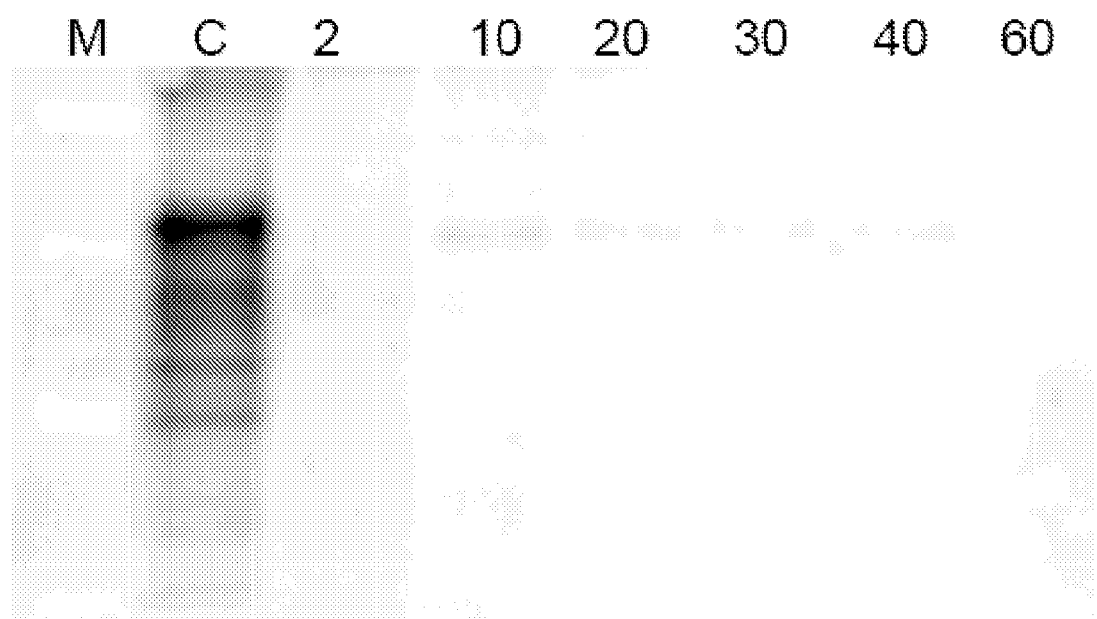
FIG. 2. A Western blot of the data generated in Example 4 showing the efficacy of decontamination using optimized enzyme concentrations for the proteolytic degradation of PrP$^{Sc}$ in conjunction with an oxidizing agent (PERASAFE™ Sterilant) at 40° C. Marker lane is labeled as M; the control lane, C, contains 12 µL of a 10% w/v brain homogenate as a control. Six lanes, as identified by incubation times, were loaded with 12 µL of 10% w/v brain homogenate treated at 40° C. for 2, 10, 20, 30, 40, and 60 minutes.
Figure 3:
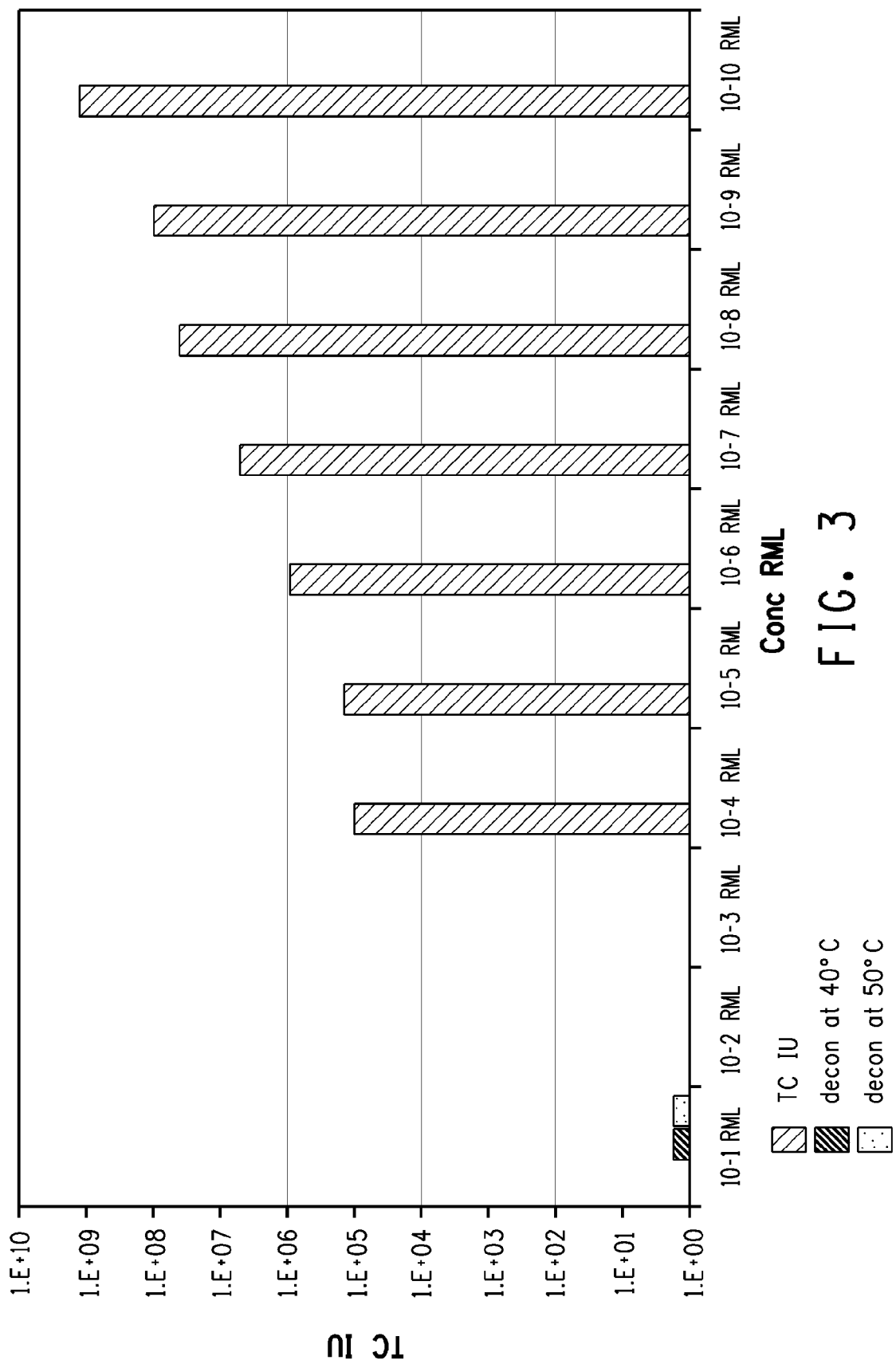
FIG. 3. A graph of the Scrapie Cell Assay (the cell culture assay described in Example 5). Various dilutions of brain homogenate from infected animals with RML (Rocky Mountain Laboratories) strains of prions are coated on wires. The wires are subjected to the decontamination treatment. Treatments at 40° C. and 50° C. were assayed. Various dilutions (RML) were plotted against the number of tissue culture infectious units (TC IU).
Figure 4:
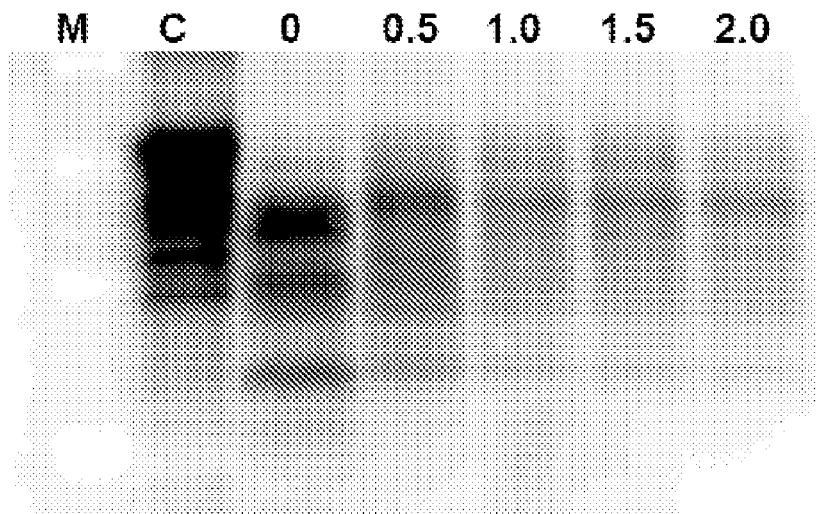
FIG. 4. A Western blot of the data generated in Example 6 showing the efficacy of decontamination using optimized enzyme concentrations for the proteolytic degradation of PrP$^{Sc}$ using various concentrations of SDS in the absence of the oxidizing agent (PERASAFE™ Sterilant) at 50° C. Marker lane is labeled as M. The control lane, C, contains 12 µL of a 10% w/v brain homogenate as a control. Lanes were loaded with 12 µL of 10% w/v brain homogenate treated at 0, 0.5, 1.0, 1.5, and 2.0% (w/v) SDS. The lanes are identified by the SDS concentration.
Figure 5:
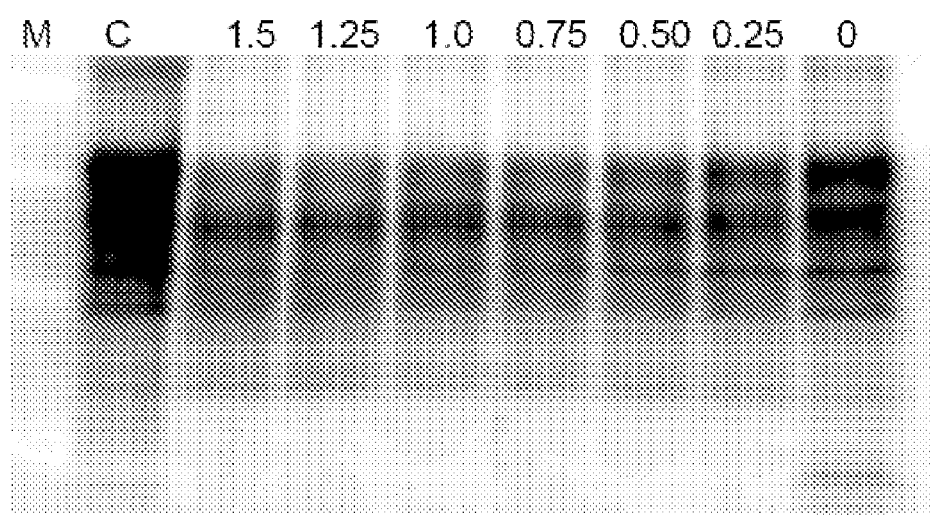
FIG. 5. A Western blot of the data generated in Comparative Example A showing the efficacy of decontamination using various ALCALASE® concentrations for the proteolytic degradation of PrP$^{Sc}$ in the absence of an oxidizing agent (PERASAFE™ Sterilant) at 50° C. Marker lane is labeled as M. The control lane, C, contains 17 μL of a 10% w/v brain homogenate as a control. Lanes were loaded with 17 μL of 10% w/v brain homogenate treated with various concentrations of ALCALASE®, and identified by ALCALASE® concentrations of 1.5, 1.25, 1.0, 0.75, 0.50, 0.25 and 0 mg/mL.

FIGS. 1a and 1b show the results of Western blot analyses from Protocols B and C, respectively. Oxidation treatment alone (PERASAFE™ Sterilant only—Protocol B) does not show prion destruction, but oxidation followed by protease treatment (Protocol C) is highly effective, the prion material disappearing by the 'five minutes' time point.

The '0 minutes' treatment in FIG. 1b shows less prion material than might be expected—this may be due to the procedures involved. This treatment is actually about 4 minutes, and each treatment is probably more accurately regarded as being extended by 4 minutes so '5 minutes' is approx. 9 minutes, '10 minutes' is approx. 14 minutes, and so on. Thus, 9 minutes of treatment appears to give destruction to undetectable levels, without high temperatures and without autoclaving or use of caustic or corrosive chemical treatments.

Example 3

Decontamination of Surgical Surfaces

The prion-degrading materials (oxidizing agent and proteases) produced by Protocol B of Example 2 were carried out on infected homogenate dipped steel wire segments.

Steel wires (5 mm×0.15 mm) were incubated for 30 minutes with a 20% homogenate prepared from the brain of a CD1 mouse terminally sick with Rocky Mountain Laboratories (RML) scrapie.

The wires were then treated according to the present invention and significant decontamination was observed for treatment under Protocol B.

A comparison was performed using Protocol B—use of oxidizing agent alone (PERASAFE™ Sterilant) was not effective.

Example 4

Prion-Decontamination Using an Oxidizing Agent (PERASAFE™ Sterilant) in Combination with Prion-Degrading Proteases at 40° C.

The purpose of this experiment was to determine the efficacy of decontamination using combination of proteases with PERASAFE™ Sterilant at approximately 40° C.

Protocol A of Example 1 was followed unless otherwise noted. A single reaction mixture containing 120 μL of 10% w/v brain homogenate in a total volume of 200 μL was produced. Aliquots of 20 μL were removed at various time points, quenched and subjected to Western Blot analysis in toto. Thus, 12 μL equivalents of 10% w/v brain homogenate were analyzed at each time point. A high sensitivity protocol for the Western Blot detection of PrP, with a known detection limit of 10 nL of a 10% w/v brain homogenate was used. Thus complete destruction of PrP as evidenced by a total lack of immunoreactivity is equivalent to at least a 1,200 fold reduction of infectivity.

The reaction was carried out in the presence of 1× PERASAFE™ Sterilant and 1% w/v SDS. Solid formulations of ALCALASE® and NEUTRASE® were prepared as 100 mg/mL stock solutions in water and used at final concentrations of 3.16 mg/mL and 12.63 mg/mL, respectively.

The reaction mixture was incubated at 40° C. with 20 μL samples removed for analysis at times 2, 10, 20, 30, 40 and 60 minutes. Residual $PrP^{Sc}$ was visualized by Western Blot detection using biotinylated anti-PrP monoclonal antibody ICSM35 as the primary antibody as shown in FIG. 2. Column headings indicate M for Marker lane, C for control lane and the incubation times as the remaining lanes. Inspection of the blot in FIG. 2, indicates that complete destruction (>1,200 fold) was achieved after 10 minutes at 40° C.

Example 5

Efficacy of Decontamination Using a Cell-Culture Assay of Prion Infectivity

The efficacy of decontamination was assayed in a cell-culture assay (a Scrapie Cell Assay; SCA). A prion-decontaminating composition containing 1× PERASAFE™ Sterilant and 1% w/v SDS and a mixture of ALCALASE® and NEUTRASE® at final concentrations of 3.16 mg/mL and 12.36 mg/mL was used. The composition was used at both 40° C. and 50° C. with a contact time of 10 minutes.

In this assay stainless steel wires were coated with various dilutions of brain homogenate from animals infected with the RML (Rocky Mountain Laboratories) strain of prions (see, Example 3). The wires were then either treated with the decontamination reagent or used untreated. They were incubated with a highly susceptible cell line (N2a-PK1; a murine neuroblastoma cell line) cloned to be highly susceptible to RML prions (see Klöhn et al., *PNAS,* 100: 11666-11671 (2003)). Following several rounds of cell-growth and dilution the cells were filtered and subjected to the MRC Prion Unit standard Scrapie Cell Assay (SCA; Klöhn et al., supra) to quantify the number of tissue culture infectious units present.

The dilution of RML proteins applied to the wires was plotted with respect to the number of tissue culture infectious units (TC IU). The results of the assay are shown in FIG. 3. As can be seen from FIG. 3, complete destruction of contaminants (>109 fold) was achieved after 10 minutes at 40° C. and 50° C. (decon at 40° C. and decon at 50° C., respectively).

Example 6

Optimization of Sodium Dodecyl Sulfate Concentration with Reagents Tested in Examples 4 and 5

The purpose of this example is to repeat the experiment as described in Example 4 with varying concentrations of surfactant (SDS) in the absence of the oxidizing agent.

A basic protocol used raw 10% w/v brain homogenate. Individual reactions mixtures containing 12 μL of 10% w/v brain homogenate in the presence of ALCALASE®/NEUTRASE® and varying concentrations (0, 0.5, 1.0, 1.5, and 2.0% w/v) of SDS in a total volume of 20 μL were produced. Aliquots were subjected to Western Blot analysis in toto. Thus, 12 μL equivalents of 10% w/v brain homogenate were analyzed at each time point.

The reactions were carried out in the presence of 3.16 mg/mL ALCALASE® and 12.63 mg/mL NEUTRASE®. The reaction mixture was incubated at 50° C. for 10 minutes. Residual $PrP^{Sc}$ was visualized by western blot detection using biotinylated ICSM35 as the primary antibody. The high sensitivity protocol for the Western blot detection of PrP was used (with a known detection limit of 10 nL of a 10% w/v brain homogenate). Complete destruction of PrP as evidenced by a total lack of immunoreactivity is equivalent to at least a >1,200 fold reduction of infectivity, which is shown in FIG. 4. As show in FIG. 4, in the absence of PERASAFE™ Sterilant, no condition gave complete destruction. As such, an SDS concentration of 1% w/v appears optimal.

Comparative Example A

Optimization of ALCALASE® Concentration in the Absence of PERASAFE™ Sterilant A basic protocol used raw 10% w/v brain homogenate. Each reaction mixture was prepared to provide a total volume of 20 μL, containing 17 μL of 10% w/v brain homogenate. The reaction mixtures contained 1% w/v SDS, 5 mg/mL NEUTRASE® and a range of ALCALASE® concentrations from 1.5 mg/mL to 250 μg/mL. The reaction mixtures were incubated at 50° C. for 10 minutes. A high sensitivity protocol for the Western Blot detection of PrP, with a known detection limit of 10 nL of a 10% w/v brain homogenate was used. Thus, complete destruction of PrP was evidenced by a total lack of immunoreactivity, which is equivalent to at least a 1,700 fold reduction of infectivity.

Residual $PrP^{Sc}$ was visualized by Western Blot detection using biotinylated ICSM35 as the primary antibody, which is shown in FIG. 5. The lanes are identified as M for marker lane, C for control and 1.5, 1.25, 1.0, 0.75, 0.50, 0.25 and 0, based on the concentrations of ALCALASE® used, concentrations in mg/mL. As shown in FIG. 5, in the absence of an oxidizing agent (i.e., PERASAFE™ Sterilant), the tested reagents showed low efficacy at 50° C. over 10 minutes.

Comparative Example B

Optimization of NEUTRASE® Concentration in the Absence of PERASAFE™ Sterilant

A basic protocol used raw 10% w/v brain homogenate. Each reaction mixture was prepared to provide a total volume of 20 µL containing 17 µL of 10% w/v brain homogenate. The reaction mixtures contained 1% w/v SDS, 1.5 mg/mL ALCALASE® and a range of NEUTRASE® concentrations from 1.5 g/mL to 250 µg/mL. The reaction mixtures were incubated at 50° C. for 10 minutes. A high sensitivity protocol for the Western Blot detection of PrP, with a known detection limit of 10 nL of a 10% w/v brain homogenate was used. Thus, complete destruction of PrP was evidenced by a total lack of immunoreactivity, which is equivalent to at least a 1,700 fold reduction of infectivity.

Figure 6:
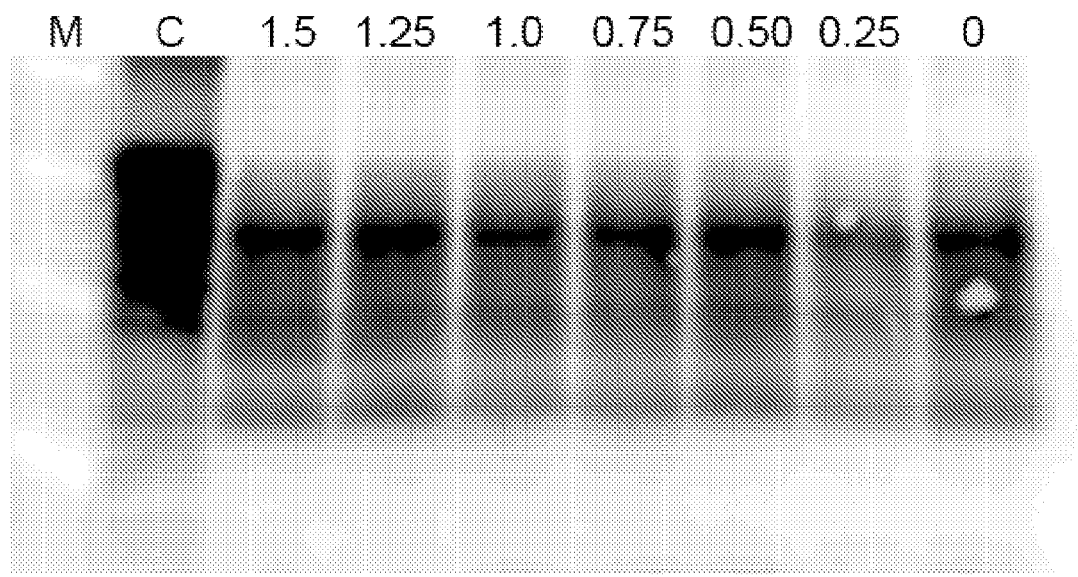
FIG. 6. A Western Blot of the data generated in Comparative Example B showing the efficacy of decontamination using various NEUTRASE® concentrations for the proteolytic degradation of PrP$^{Sc}$ in the absence of an oxidizing agent (PERASAFE™ Sterilant) at 50° C. Marker lane is labeled as M. The control lane, C, contains 17 μL of a 10% w/v brain homogenate as a control. Lanes were loaded with 17 μL of 10% w/v brain homogenate treated with various concentrations of NEUTRASE® and identified by NEUTRASE® concentrations of 1.5, 1.25, 1.0, 0.75, 0.50, 0.25 and 0 mg/mL.

Residual PrP$^{Sc}$ was visualised by Western Blot detection using biotinylated ICSM35 as the primary antibody, which is shown in FIG. 6. The lanes are identified as M for marker lane, C for control and 1.5, 1.25, 1.0, 0.75, 0.50, 0.25 and 0, based on the concentrations of NEUTRASE® used, concentrations in mg/mL. As shown in FIG. 6, in the absence of oxidizing agent (e.g., PERASAFE™ Sterilant), the tested reagents showed low efficacy at 50° C. over 10 minutes.

Example 7

Optimization of NEUTRASE®/ALCALASE® Concentrations in the Presence of PERASAFE™ Sterilan The purpose of this experiment was to show that the rate of enzyme inclusion could be substantially reduced when used in combination with PERASAFE™ Sterilant.

A basic protocol used raw 10% w/v brain homogenate. Each reaction mixture was prepared to provide a total volume of 100 µL containing 60 µL of 10% w/v brain homogenate. The reaction mixtures contained 1× PERASAFE™ Sterilant, 1% w/v SDS and range of ALCALASE® and NEUTRASE® concentrations (as measured by relative dilution rates; 2×, 4×, 8×, 16×, 32×, and 64× dilutions). The reaction mixtures were incubated at 50° C. for 10 minutes and 40 µL of each reaction mixture was analyzed. A high sensitivity protocol for the Western Blot detection of PrP, with a known detection limit of 10 nL of a 10% w/v brain homogenate was used. Thus, complete destruction of PrP was evidenced by a total lack of immunoreactivity, which is equivalent to at least a 1,200 fold reduction of infectivity.

Figure 7:
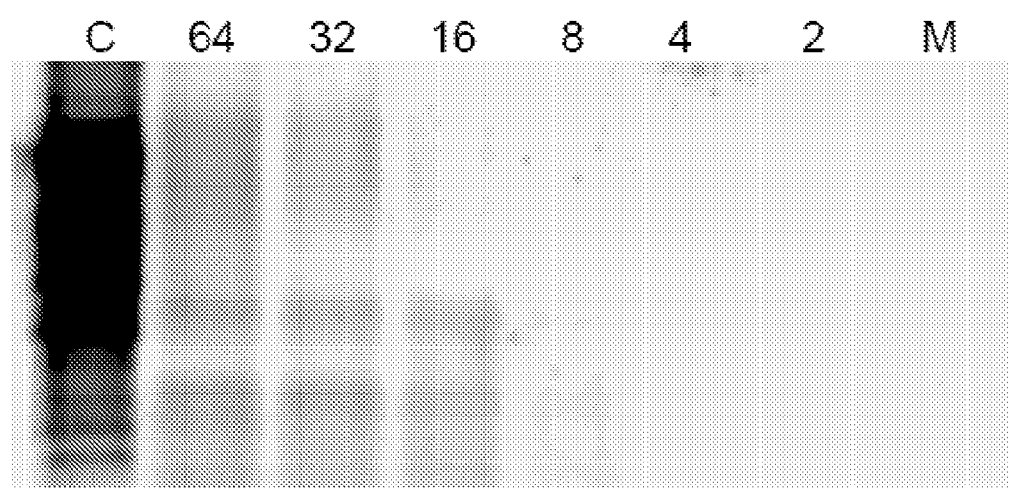
FIG. 7. A Western blot of the data generated in Example 7 showing the efficacy of decontamination using various ALCALASE®/NEUTRASE® concentrations (based on a fold dilution from previous examples; 2, 4, 8, 16, 32, 64-fold dilutions) for the proteolytic degradation of PrP$^{Sc}$ in the presence of an oxidizing agent (PERASAFE™ Sterilant) at 50° C. Marker lane is labeled as M. The control lane, C, contains 12 μL of a 10% w/v brain homogenate as a control. Lanes labeled 64, 32, 16, 8, 4, and 2 were loaded with 12 μL of 10% w/v brain homogenate and the respective dilutions of ALCALASE®/NEUTRASE®. For example, the lane marked as 2 is a 2-fold dilution of the standard ALCALASE®/NEUTRASE® concentrations (i.e. 1.58 mg/mL ALCALASE® and 6.32 mg/mL NEUTRASE®).

Residual PrP$^{Sc}$ was visualized by Western Blot detection using biotinylated ICSM35 as the primary antibody, which is shown in FIG. 7. The lanes are identified as M for marker lane, C for control and 64, 32, 16, 8, 4, 2 and 0, based on the dilution factors of protease concentrations used. As shown in FIG. 7, the greatest destruction occurred in the lane marked 2. This is a 2-fold dilution of the standard ALCALASE®/NEUTRASE® concentrations (i.e., 1.58 mg/mL ALCALASE® and 6.32 mg/mL NEUTRASE®). As a result, high levels of destruction can be achieved at enzyme concentrations 8-fold lower than previously tested in cell-culture assays. The level of destruction is at least 1000-fold. Effective decontamination at 50° C. for 10 minutes in the presence of PERASAFE™ Sterilant with 1% w/v SDS and enzyme concentrations of 400 µg/mL and 1.6 mg/mL ALCALASE® and NEUTRASE®, respectively.

Example 8

Further Optimization of ALCALASE®/NEUTRASE® Concentrations in the Presence of PERASAFE™ Sterilant A basic protocol used raw 10% w/v brain homogenate. Each reaction mixture was prepared to provide a total volume of 100 µL containing 60 µL of 10% w/v brain homogenate. The reaction mixtures contained 1× PERASAFE™ Sterilant, 1% w/v SDS and range of ALCALASE® and NEUTRASE® concentrations at various dilutions (4 [790 µg/mL ALCALASE®+3.16 mg/mL NEUTRASE®], 6.7 [474 µg/mL ALCALASE®+1.89 mg/mL NEUTRASE®], 8.3 [379 µg/mL ALCALASE®+1.52 mg/mL NEUTRASE®], 10 [316 µg/mL ALCALASE®+1.26 mg/mL NEUTRASE®], and 12.5 [253 µg/mL ALCALASE®+1.01 mg/mL NEUTRASE®]. The reaction mixtures were incubated at 50° C. for 10 minutes and 40 µL of each reaction was analyzed. A high sensitivity protocol for the Western Blot detection of PrP, with a known detection limit of 10 nL of a 10% w/v brain homogenate was used. Thus complete destruction of PrP was evidenced by a total lack of immunoreactivity, which is equivalent to at least a 1,200 fold reduction of infectivity.

Figure 8:
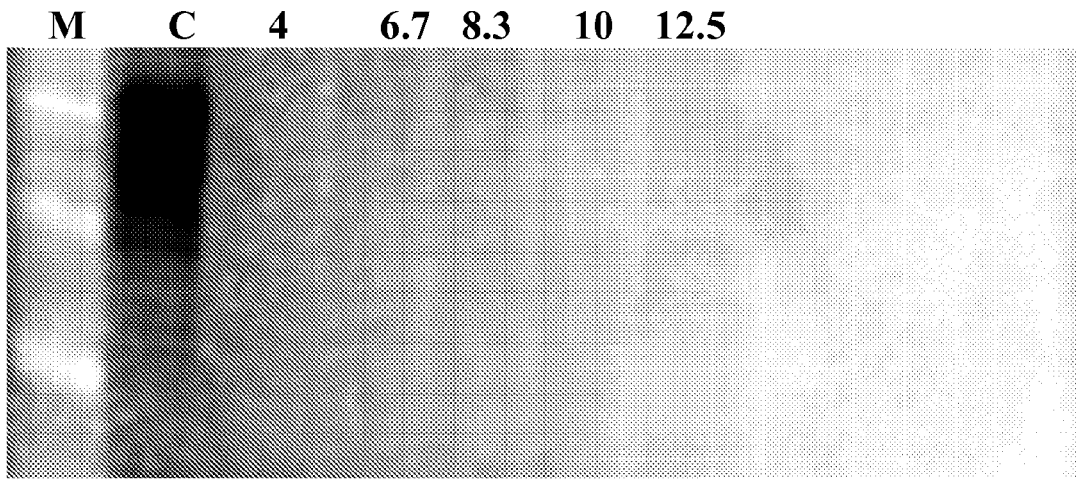
FIG. 8. A Western blot of the data generated in Example 8 showing the efficacy of decontamination using various ALCALASE®/NEUTRASE® concentrations (based on fold dilutions of 4, 6.7, 8.3, 10, and 12.5). Each lane is identified by the dilution factor, shown as lane labels, for the proteolytic degradation of PrP$^{Sc}$ in the presence of an oxidizing agent (PERASAFE™ Sterilant) at 50° C. Marker lane is labeled as M. The control lane, C, contains 12 μL of a 10% w/v brain homogenate as a control. Lanes labeled 4, 6.7, 8.3, 10 and 12.5 were loaded with 12 μL of 10% w/v brain homogenate and the respective dilutions of ALCALASE®/NEUTRASE®.

Residual PrP$^{Sc}$ was visualised by Western Blot detection using biotinylated ICSM35 as the primary antibody, which is shown in FIG. 8. The lanes are identified as M for marker lane, C for control and 4, 6.7, 8.3, 10, and 12.5, based on the dilution factors of protease concentrations used. As shown in FIG. 8, high levels of destruction can be achieved at ALCALASE® and NEUTRASE® concentrations 10-fold lower than previously tested in cell-culture.

Comparative Example C

Testing of Individual Components that Comprise PERASAFE™ Sterilant with SDS and Enzymes A basic protocol used raw 10% w/v brain homogenate. Each reaction mixture was prepared to provide a total volume of 20 µL containing 16 µL of 10% w/v brain homogenate. The reaction mixtures contained 1% w/v SDS, 750 g/mL ALCALASE®, 3 mg/mL NEUTRASE® plus various components of PERASAFE™ Sterilant.

| Lane | Component |
|------|-----------|
| (a) | Stabilizers/Corrosion Inhibitors (191 µg/mL) |
| (b) | Surfactant (165 µg/mL) |
| (c) | Organic Acid (3.36 mg/mL) |
| (d) | Activator (4.44 mg/mL) |
| (e) | Oxidizing Agent (8.03 mg/mL) |
| (f) | Water (control) |

The reactions were incubated at 50° C. for 10 minutes and 40 µL of each reaction was analyzed. A high sensitivity protocol for the Western Blot detection of PrP, with a known detection limit of 10 nL of a 10% w/v brain homogenate was used. Thus, complete destruction of PrP was evidenced by a total lack of immunoreactivity, which is equivalent to at least a 1,600 fold reduction of infectivity.

Figure 9:
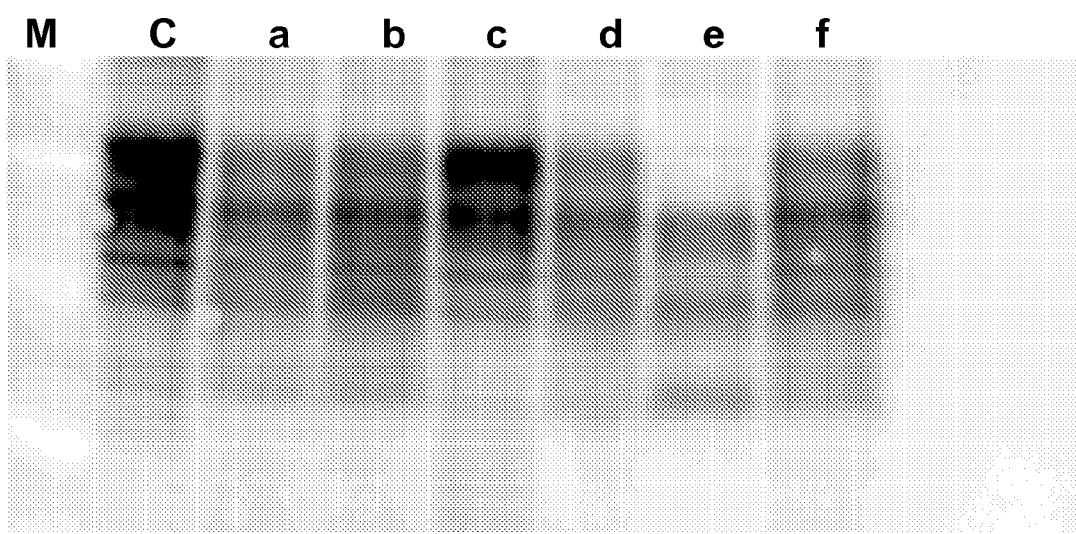
FIG. 9. A Western blot of the data generated in Comparative Example C showing the efficacy of decontamination using components of PERASAFE™ Sterilant formulation components in combination with 1% w/v SDS, 750 μg/mL ALCALASE® and 3 mg/mL NEUTRASE® at 50° C. Marker lane is labeled as M. The control lane, C, contains 16 μL of a 10% w/v brain homogenate as a control. Lanes labeled (a) through (f) were loaded with 16 μL of 10% w/v brain homogenate and the respective components as identified in Comparative Example C.
Figure 10:
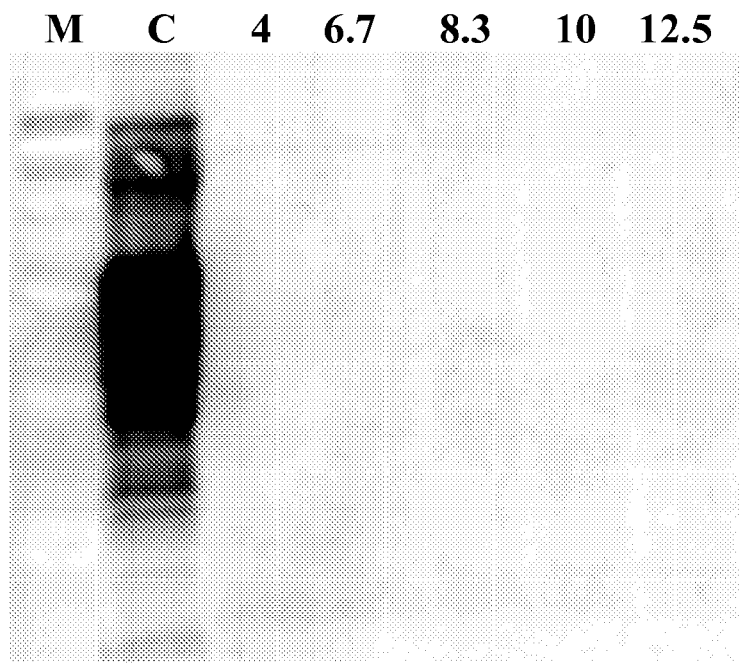
FIG. 10. A Western blot of the data generated in Example 9 showing the efficacy of decontamination using various ALCALASE®/NEUTRASE® concentrations (based on fold dilutions of 4, 6.7, 8.3, 10, and 12.5). Each lane is identified by the dilution factor, shown as lane labels, for the proteolytic degradation of PrP$^{Sc}$ in the presence of an oxidizing agent (PERASAFE™ Sterilant) at 50° C. This is a repeat of the work original performed in Example 8 (FIG. 8). Marker lane is labeled as M. The control lane, C, contains 12 μL of a 10% w/v brain homogenate as a control. Lanes labeled 4, 6.7, 8.3, 10, and 12.5 were loaded with 12 μL of 10% w/v brain homogenate and the respective dilutions of ALCALASE®/NEUTRASE®.
Figure 11:
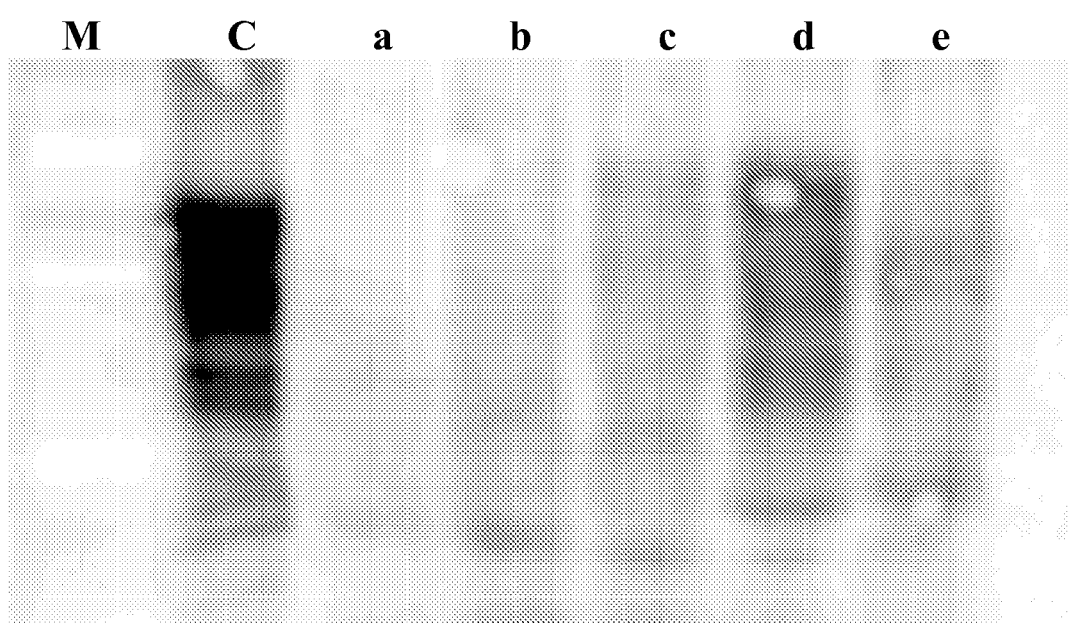
FIG. 11. A Western blot of the data generated in Example 10 showing the efficacy of decontamination using various components of PERASAFE™ Sterilant or dilutions of complete PERASAFE™ Sterilant relative to the standard 1× formulation in combination with 1% w/v SDS, 330 μg/mL ALCALASE® and 1.2 mg/mL NEUTRASE® at 50° C. Marker lane is labeled as M. The control lane, C, contains 13 μL of a 10% w/v brain homogenate as a control. Lanes labeled (a) through (e) were loaded with 13 μL of 10% w/v brain homogenate and the respective components as indicated in Example 10.
Figure 12:
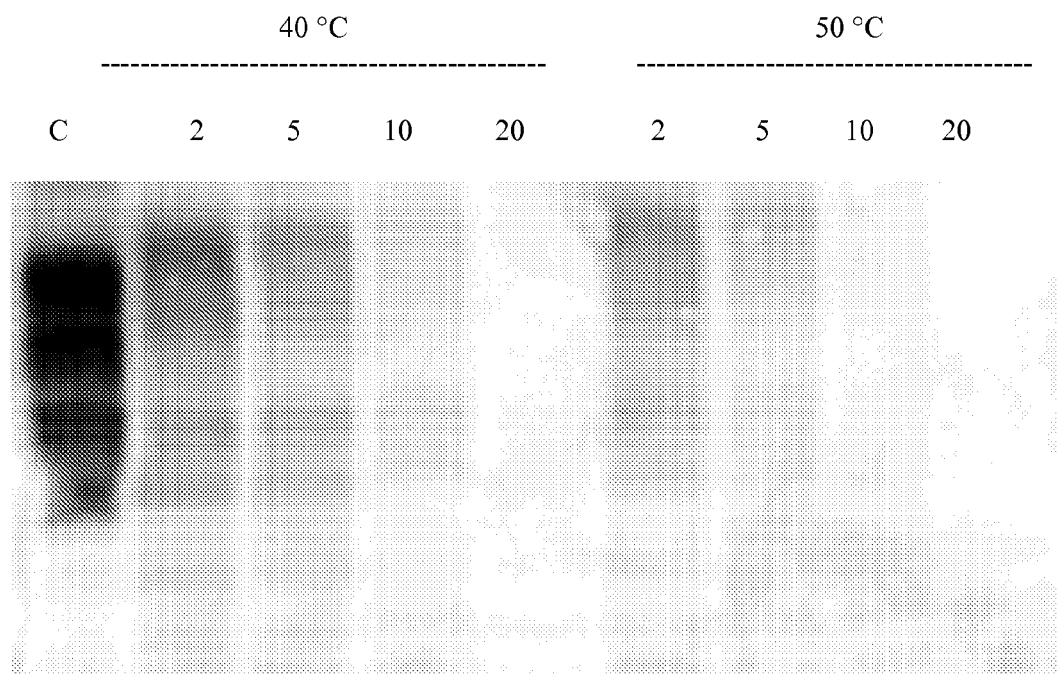
FIG. 12. Western blot of the data generated in Example 11 showing the efficacy of 1× PERASAFE™ Sterilant+1% w/v SDS+ALCALASE®+NEUTRASE® for decontamination of prions at 40° C. vs. 50° C. The control lane, C, contains 12 μL of a 10% w/v brain homogenate as a control. Lanes 2, 5, 10, and 20 at each temperature indicate the reaction times. These lanes were loaded with 12 μL of 10% w/v brain homogenate treated at the temperatures and times indicated.
Figure 13:
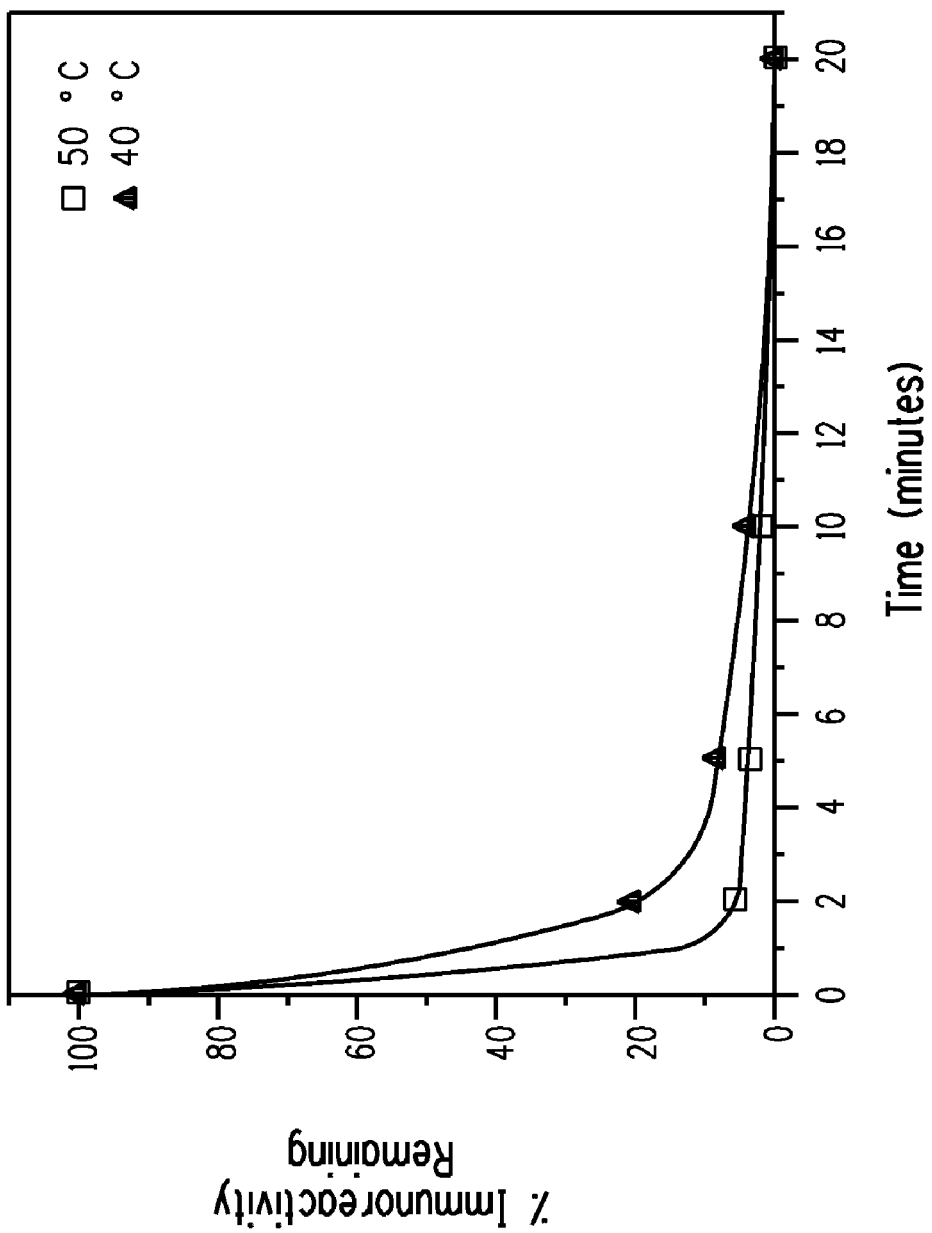
FIG. 13. Graphical comparison of PrP degradation kinetics at 40° C. and 50° C. from the Western blot of FIG. 12 and data generated in Example 11. The data are best described by a double exponential decay due to the two main species of PrP present; PrP$^C$ and PrP$^{Sc}$. The $K_{1/2}$ values are very similar for both 40° C. and 50° C. (29 seconds and 22 seconds, respectively).

Residual PrP$^{Sc}$ was visualised by Western Blot detection using biotinylated ICSM35 as the primary antibody, as shown in FIG. 9. The lanes are identified as M for marker lane, C for control and a-f, based on the component identified above. FIG. 9 shows no single component produced levels of destruction comparable to those observed with active PERASAFE™ Sterilant (e). It appears that efficacy is result of the oxidative activity provided by the peracetic acid generated from TAED/sodium perborate. However, when combined with proteases in the compositions of this invention, significantly improved prion destruction is achieved.

Example 9

Repeat of the Optimization of ALCALASE®/NEUTRASE® Concentrations in the Presence of PERASAFE™ Sterilant The experiment described in Example 8 was repeated to confirm a 10-fold reduction in enzyme levels in the formulation was effective when enzymes were combined with oxidizing agent.

A basic protocol used raw 10% w/v brain homogenate. Each reaction mixture was prepared to provide a total volume of 100 μL containing 60 μL of 10% w/v brain homogenate. The reaction mixtures contained 1× PERASAFE™ Sterilant, 1% w/v SDS and range of ALCALASE® and NEUTRASE® concentrations (4 [790 μg/mL ALCALASE®+3.16 mg/mL NEUTRASE®], 6.7 [474 μg/mL ALCALASE®+1.89 mg/mL NEUTRASE®], 8.3 [379 μg/mL ALCALASE®+1.52 mg/mL NEUTRASE®], 10 [316 μg/mL ALCALASE®+1.26 mg/mL NEUTRASE®], and 12.5 [253 μg/mL ALCALASE®+1.01 mg/mL NEUTRASE®]. The reaction mixtures were incubated at 50° C. for 10 minutes and 40 μL of each reaction was analyzed. A high sensitivity protocol for the Western Blot detection of PrP, with a known detection limit of 10 nL of a 10% w/v brain homogenate was used. Thus, complete destruction of PrP was evidenced by a total lack of immunoreactivity, which is equivalent to at least a 1,200 fold reduction of infectivity.

Residual $PrP^{Sc}$ was visualised by Western Blot detection using biotinylated ICSM35 as the primary antibody, as shown in FIG. 10. The lanes are identified as M for marker lane, C for control and 4, 6.7, 8.3, 10, and 12.5, based on the dilution factors of protease concentrations used. FIG. 10 shows high levels of destruction can be achieved at ALCALASE® and NEUTRASE® concentrations at least 10-fold lower than previously tested in cell culture. FIG. 10 confirms the previous findings of Example 8.

Example 10

Further Testing of Individual Components that Comprise PERASAFE™ Sterilant with SDS and Enzymes+Redox Active Combinations A basic protocol used raw 10% w/v brain homogenate. Each reaction mixture was prepared to provide a total volume of 20 μL containing 13 μL of 10% w/v brain homogenate. The reaction mixtures contained 1% w/v SDS, 300 μg/mL ALCALASE®, 1.2 mg/mL NEUTRASE® plus various components or concentrations of PERASAFE™ Sterilant.

| Lane | Component |
|---|---|
| (a) | PERASAFE ™ Sterilant (16.2 g/L) (1X) |
| (b) | PERASAFE ™ Sterilant (8.1 g/L) (0.5X) |
| (c) | PERASAFE ™ Sterilant (3.24 g/L) (0.2X) |
| (d) | Stabilizers/Corrosion Inhibitors (191 μg/mL) |
| (e) | Sodium Perborate + Activator (8.03 mg/mL) |

The reactions were incubated at 50° C. for 10 minutes and 40 μL of each reaction was analyzed. A high sensitivity protocol for the Western Blot detection of PrP, with a known detection limit of 10 nL of a 10% w/v brain homogenate was used. Thus, complete destruction of PrP was evidenced by a total lack of immunoreactivity, which is equivalent to at least a 1,300 fold reduction of infectivity.

Residual $PrP^{Sc}$ was visualised by Western Blot detection using biotinylated ICSM35 as the primary antibody, as shown in FIG. 11. The lanes are identified as M for marker lane, C for control and a-e, based on the component identified above. FIG. 11 shows high levels of destruction were confirmed with 1× PERASAFE™ Sterilant in the presence of 1% w/v SDS, 300 μg/mL ALCALASE® and 1.2 mg/mL NEUTRASE®. It appears that a reduced inclusion rate of 0.5× PERASAFE™ Sterilant may provide sufficient levels of decontamination.

Example 11

Comparing the Efficacy of Decontamination by the 1× PERASAFE™ Sterilant based Decontamination Composition at 40° C. and 50° C.

The purpose of the following experiment was to compare the efficacy of decontamination by the decontamination composition (1× PERASAFE™ Sterilant+1% w/v SDS+300 μg/mL ALCALASE®+1.2 mg/mL NEUTRASE®) at 40° C. and 50° C.

A basic protocol used raw 10% w/v vCJD brain homogenate. A reaction mixture containing 60 μl of 10% w/v brain homogenate in a total volume of 100 μl was used for each temperature. The reaction mixtures contained an equivalent formulation of the decontamination mixture [1× PERASAFE™ Sterilant and 1% w/v SDS+300 μg/mL ALCALASE®+1.2 mg/mL NEUTRASE®]. Aliquots of 20 μL were removed at various time points, quenched by adding to 2×SDS loading buffer and freezing in liquid nitrogen. All reaction mixtures were thawed and boiled before subjecting to Western Blot detection for residual $PrP^{Sc}$ using biotinylated ICSM35 as the primary antibody.

The reaction mixtures (40° C. vs. 50° C.) were sampled at time 0, 2, 5, 10 and 20 minutes and the results are shown in FIG. 12, with the sample times as the lane labels. C is for control. The levels of immunoreactivity in FIG. 12 were quantified by densitometry and plotted as function of time in FIG. 13. The kinetic curves describing the loss of PrP, % Immunoreactivity Remaining, with respect to time in minutes, were fitted to double exponential decay functions and the results superimposed as lines through the data in FIG. 13. A slight reduction in rate of destruction is observed at 40° C. than 50° C. However, very high levels of destruction are achieved after 10 min incubation time at both temperatures.

Example 12

Comparison of Oxidizing Agents with PERASAFE™ Sterilant as Additives to Composition to Decontaminate Infected Entities The purpose of the following examples was to compare chemical oxidizing agents for use in a decontamination composition comprising SDS (1% w/v) and two prion-degrading proteases (300 μg/mL ALCALASE® and 1.2 mg/mL NEUTRASE®). The oxidizing agents included NaDCC (sodium dichloroisocyanurate), PROXITANE® (a peracetic acid-based disinfectant available from Solvay Chemicals, Brussels, Belgium), VIRKON® S Disinfectant (a disinfectant comprising potassium peroxymonosulfate and NaCl, sodium dodecylbenzene sulfonate, and sulfamic acid), hypochlorite solution (i.e., bleach), and PERASAFE™ Sterilant.

A basic protocol used raw 10% w/v vCJD brain homogenate. Each reaction mixture was prepared using 60 μL of 10% w/v brain homogenate in a total volume of 100 μL. Constant concentrations of SDS and enzymes [1% w/v SDS and 300 μg/mL ALCALASE®+1.2 mg/mL NEUTRASE®] were used in all of the reaction mixtures and all reaction mixtures were incubated for 10 minutes at 50° C.

Reaction A contained 16.2 mg/mL standard PERASAFE™ Sterilant.

Reaction B contained 13.0 mg/mL standard PERASAFE™ Sterilant.

Reaction C contained 13.0 mg/mL standard PERASAFE™ Sterilant.

Reaction H contained a 1:70 dilution of hypochlorite solution (i.e., bleach), (pH 8.0).

Reaction N contained 3.34 mg/mL NaDCC.

Reaction P contained 30 mg/mL PROXITANE® (pH 6.5).

Reaction V contained 20 mg/mL VIRKON® S (pH 6.0).

Figure 14:
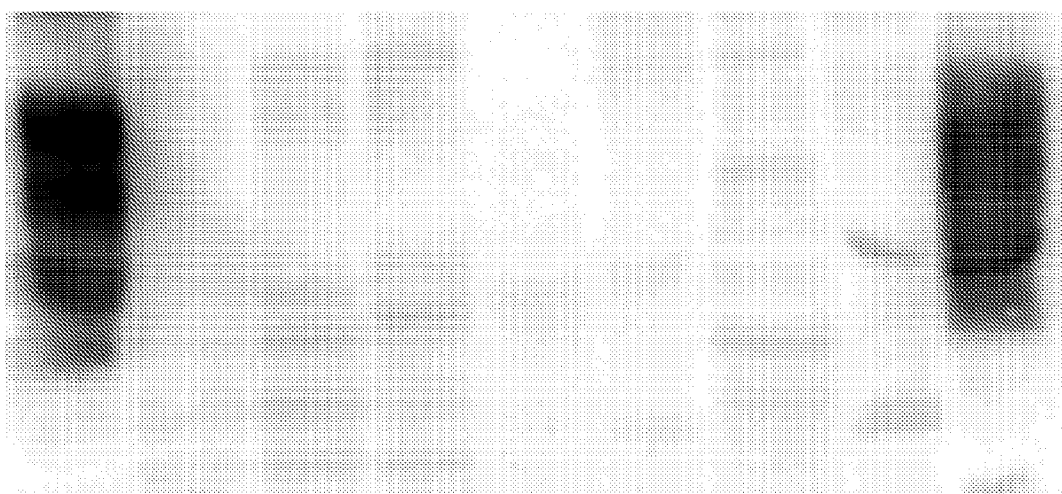
FIG. 14. Western blot of the data generated in Example 12 comparing the efficacy of other oxidizing agents when used in combination with 1% w/v SDS and 300 μg/mL ALCALASE®+1.2 mg/mL NEUTRASE®. The control lane, C, contains 12 μL of a 10% w/v brain homogenate as a control. Lanes labelled "A", "B", "C", "H", "N", "P", and "V") were loaded with 12 μL of 10% w/v brain homogenate treated as described. C=control, A=16.2 mg/mL PERASAFE™ Sterilant (1×), B and C=13 mg/mL PERASAFE™ Sterilant (0.8×), H=a 1:70 dilution of hypochlorite (pH 8), N=3.34 mg/mL NaDCC (Neochlor), P=30 mg/mL PROXITANE® (pH 6.5), and V=20 mg/mL VIRKON® S Disinfectant (pH 6).

Aliquots of 20 μL were removed after 10 minutes incubation and quenched by adding to 2×SDS loading buffer and freezing in liquid nitrogen. All reaction mixtures were thawed and boiled before subjecting to Western Blot detection for residual PrP$^{Sc}$ using biotinylated ICSM35 as the primary antibody. The results are shown in FIG. 14. The lanes on the gel correspond to the reactions listed above.

Figure 15:
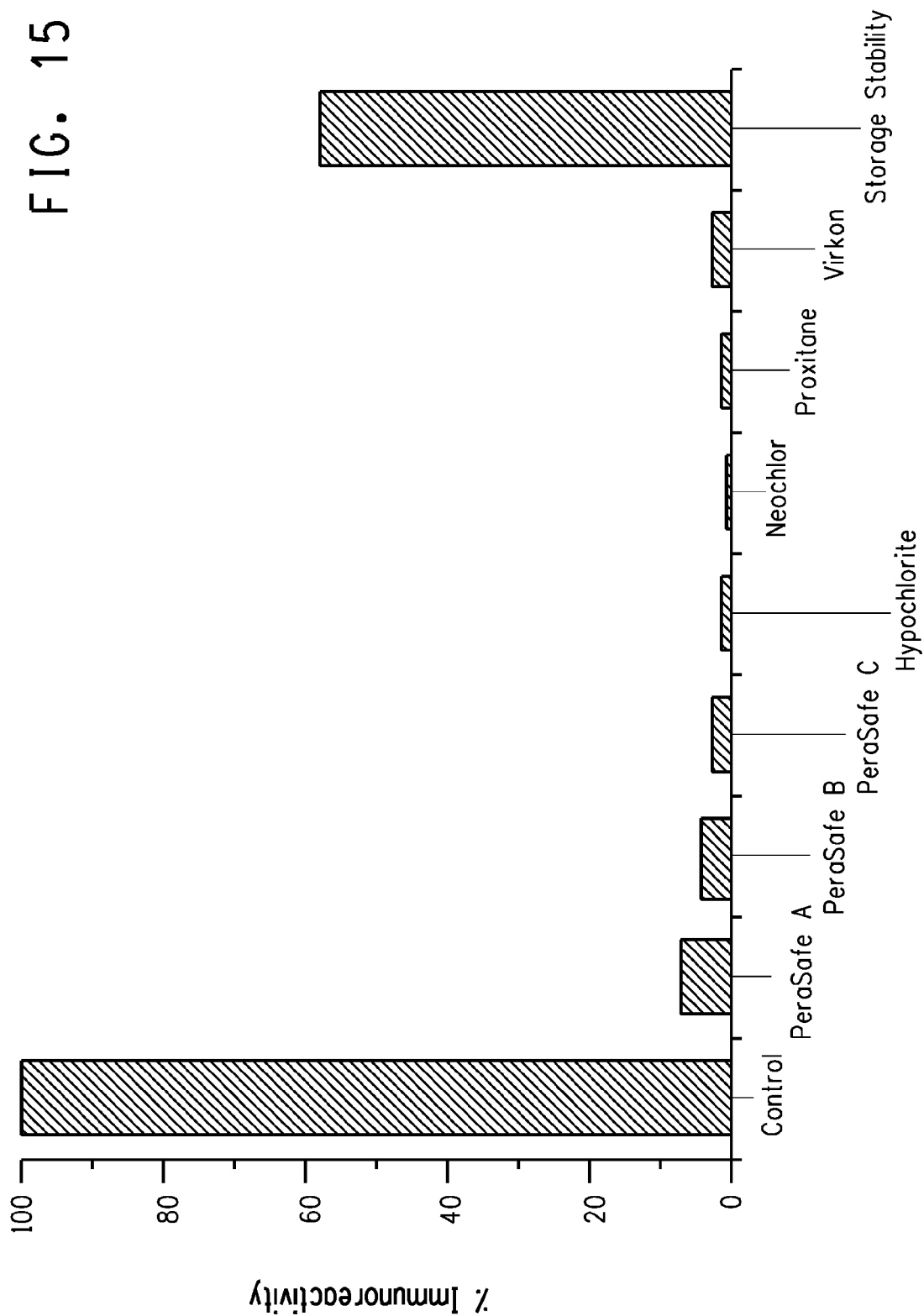
FIG. 15. A graphical representation of the levels of immunoreactivity shown in FIG. 14 based on data generated in Example 12. The lanes shown in FIG. 14 were quantified by densitometry and are displayed below as a percentage of the control value.

As shown in FIG. 14, other oxidizing agents are effective when used as the oxidizing agent in a decontamination composition comprising surfactant and the two different prion-degrading proteases. The levels of immunoreactivity in FIG. 14 were quantified by densitometry and are displayed as a percentage of the control value, % Immunoreactivity, in FIG. 15.

What is claimed is:

1. A method for degrading prions on a prion-contaminated surface comprising contacting the prion-contaminated surface with a prion-degrading composition comprising:
    (a) a non-enzymatic peroxygen-generating component:
        (i) perborate or percarbonate; and
        (ii) tetraacetyl ethylene diamine (TAED) or N-acetyl caprolactam;
    (b) at least one protease; and
    (c) at least one surfactant;
wherein the contacting is performed under suitable conditions and a period of time sufficient to degrade the prions on the prion-contaminated surface.

2. The method for degrading prions on a prion-contaminated surface of any of claim 1, wherein the at least one protease comprises Neutrase isolated from *Bacillus amyloliquifaciens* or Alcalase isolated from *Bacillus licheniformis*.

3. The method for degrading prions on a prion-contaminated surface of any of claim 1, wherein the at least one surfactant is sodium dodecyl sulfate.

* * * * *